(12) United States Patent
Flood et al.

(10) Patent No.: US 11,540,759 B2
(45) Date of Patent: Jan. 3, 2023

(54) BIOSIGNAL HEADPHONES

(71) Applicant: MINDSET INNOVATION INC., Brossard (CA)

(72) Inventors: Jacob Flood, Brossard (CA); David Doyon, Saint-Constant (CA); Warren Robinson, Toronto (CA); Xin Yao, Brossard (CA); Christopher Faust, Saint-Laurent (CA)

(73) Assignee: Mindset Innovation Inc., Brossard (CA)

( * ) Notice: Subject to any disclaimer, the term of this patent is extended or adjusted under 35 U.S.C. 154(b) by 950 days.

(21) Appl. No.: 16/337,850

(22) PCT Filed: Sep. 29, 2017

(86) PCT No.: PCT/CA2017/051162
§ 371 (c)(1),
(2) Date: Mar. 28, 2019

(87) PCT Pub. No.: WO2018/058253
PCT Pub. Date: Apr. 5, 2018

(65) Prior Publication Data
US 2020/0029881 A1 Jan. 30, 2020

Related U.S. Application Data

(60) Provisional application No. 62/401,263, filed on Sep. 29, 2016.

(51) Int. Cl.
*A61B 5/16* (2006.01)
*H04R 1/10* (2006.01)
(Continued)

(52) U.S. Cl.
CPC .............. *A61B 5/168* (2013.01); *A61B 5/291* (2021.01); *A61B 5/375* (2021.01); *A61B 5/6803* (2013.01);
(Continued)

(58) Field of Classification Search
CPC ......... A61B 5/168; A61B 5/291; A61B 5/375; A61B 5/6803; A61B 5/7264;
(Continued)

(56) References Cited

U.S. PATENT DOCUMENTS 5,740,812 A * 4/1998 Cowan .................... A61B 5/38
600/545
7,081,085 B2 7/2006 Viirre et al.
(Continued)

FOREIGN PATENT DOCUMENTS

AU 2001223490 A1 1/2007
GB 1374658 A 11/1974
(Continued)

*Primary Examiner* — Oyesola C Ojo
(74) *Attorney, Agent, or Firm* — Benoit & Cote Inc.; Charles-André Caron

(57) ABSTRACT

There are described headphones comprising earcups to be placed about ears of a user, with a headband linking the earcups and to be extending above a head of the user. A flexible band distinct from the headband is secured below the headband for contact with the head of the user. Removable headband sensors are embedded in the flexible band and have a portion thereof protruding downwardly from the flexible band to reach the scalp. The flexible band has a flexibility which makes the flexible band deform under the weight of the earcups to conform with the head of the user to ensure high quality contact between the headband electrodes and the scalp. There are further provided earcup electrodes on the earcups for contact with a region on or behind an ear of the user. Signals from the electrodes can be
(Continued)

used for different purposes such as concentration monitoring and feedback.

20 Claims, 19 Drawing Sheets

(51) Int. Cl.
*A61B 5/00* (2006.01)
*A61B 5/291* (2021.01)
*A61B 5/375* (2021.01)

(52) U.S. Cl.
CPC .......... *A61B 5/7264* (2013.01); *H04R 1/105* (2013.01); *H04R 1/1008* (2013.01); *H04R 1/1041* (2013.01); *H04R 1/1058* (2013.01)

(58) Field of Classification Search
CPC .... H04R 1/1008; H04R 1/1041; H04R 1/105; H04R 1/1058; H04R 5/0335; H04R 1/1083; H04R 2201/10; H04R 2410/05
See application file for complete search history.

(56) References Cited

U.S. PATENT DOCUMENTS

| | | | |
|---|---|---|---|
| 7,865,235 B2 | 1/2011 | Le | |
| 8,548,555 B2 | 10/2013 | Jin et al. | |
| 8,731,633 B2 | 5/2014 | Asjes | |
| 8,781,570 B2 | 7/2014 | Chuang | |
| 8,798,736 B2 | 8/2014 | Sullivan et al. | |
| 10,924,869 B2 * | 2/2021 | Gallégo | A61B 5/6817 |
| 11,172,859 B2 * | 11/2021 | Connor | A61B 5/6814 |
| 2004/0122303 A1 * | 6/2004 | Kopke | A61B 5/291 |
| | | | 600/383 |
| 2004/0230549 A1 | 11/2004 | Freer et al. | |
| 2005/0043646 A1 | 2/2005 | Viirre | |
| 2007/0060831 A1 | 3/2007 | Le | |
| 2007/0106169 A1 * | 5/2007 | Fadem | A61B 5/38 |
| | | | 600/544 |
| 2007/0197292 A1 | 8/2007 | Collura | |
| 2008/0146892 A1 | 6/2008 | LeBoeuf et al. | |
| 2008/0177197 A1 | 7/2008 | Lee | |
| 2009/0099474 A1 | 4/2009 | Pineda | |
| 2010/0280338 A1 | 11/2010 | Chou | |
| 2012/0203130 A1 | 8/2012 | Bernhard | |
| 2012/0220889 A1 | 8/2012 | Sullivan | |
| 2012/0226127 A1 | 9/2012 | Asjes | |
| 2013/0039509 A1 | 2/2013 | Chuang et al. | |
| 2013/0066183 A1 | 3/2013 | Jin | |
| 2014/0140567 A1 | 5/2014 | LeBoeuf et al. | |
| 2014/0200432 A1 | 7/2014 | Banerji et al. | |
| 2014/0249360 A1 | 9/2014 | Jaeger et al. | |
| 2015/0313496 A1 | 11/2015 | Connor | |
| 2015/0342493 A1 | 12/2015 | Hardt | |
| 2016/0143554 A1 | 5/2016 | Lim et al. | |
| 2016/0210407 A1 | 7/2016 | Hwang et al. | |
| 2017/0027467 A1 | 2/2017 | Hagedorn | |
| 2017/0071495 A1 | 3/2017 | Denison et al. | |
| 2017/0339484 A1 * | 11/2017 | Kim | A61B 5/6815 |

FOREIGN PATENT DOCUMENTS

| | | | | |
|---|---|---|---|---|
| GB | 2396421 A | * | 6/2004 | .......... A61B 5/6803 |
| GB | 2396421 A | | 6/2004 | |
| GB | 2559984 A | * | 8/2018 | ......... A61B 5/04845 |
| WO | 2013038285 A1 | | 3/2013 | |
| WO | 2014074013 A1 | | 5/2014 | |
| WO | WO-2014074013 A1 | * | 5/2014 | .......... A61B 5/0478 |
| WO | 2014085910 A1 | | 6/2014 | |
| WO | 2015153744 A1 | | 10/2015 | |
| WO | 2016070188 A1 | | 5/2016 | |
| WO | 2016079525 A1 | | 5/2016 | |
| WO | 2017069644 A2 | | 4/2017 | |

* cited by examiner

BIOSIGNAL HEADPHONES

CROSS-REFERENCE TO RELATED APPLICATIONS

This application claims benefit or priority from provisional U.S. patent application 62/401,263, filed Sep. 29, 2016, the specification of which is hereby incorporated herein by reference in its entirety.

BACKGROUND

(a) Field

The subject matter disclosed generally relates to consumer-grade biosensors. More specifically, it relates to headphones with EEG sensors and a method for operating them.

(b) Related Prior Art

Electroencephalography (EEG) has been used in clinical settings in the last decades as a tool to measure brain activity. Multi-thousand-dollar, clinical-grade EEG machines use electrodes to measure voltages on the scalp, in order to infer which regions of the brain are active. Recently, more sophisticated techniques have been used to detect precise brain activity, such as responses to stimulus, and anxiety. The principle of neurofeedback presents the output of EEG brain scans as a feedback to users in order to treat a number of neurological disorders, such as depression or attention deficit disorder.

The prior art technologies are limited to laboratory settings using a 21-sensor cap, conductive paste (applied below wet electrodes), and multi-thousand-dollar clinical-grade amplifiers. Neurofeedback can be given under controlled conditions, while supervised by a trained clinician.

Clinical-grade EEG devices are 21-electrode caps, connected to standalone data acquisition consoles. Interpretation of the resulting signals requires the help of a trained clinician.

Over the last decades, EEG technology has mostly been limited to clinical use. Neurofeedback protocols are administered under the supervision of a trained clinician, for the purpose of treating a variety of medical conditions, including but not limited to anxiety disorder and attention deficit disorder. Several recent technological changes have permit the above invention to become realizable.

In addition to clinical-grade devices, the prior art technology is available as consumer-grade products. Indeed, there have been attempts to transform the case-limited clinical-grade technology into a portable device, such as a headband.

The consumer-grade EEG devices are portable, standalone bands that attach to the head of the user. These devices use internal computation to automate the role of the clinician in the neurofeedback process. Examples can be found in WO2016070188A1, WO2016079525A1, US20170027467A1, US20100280338A1, U.S. Pat. Nos. 8,731,633, 8,781,570, or 5,740,812.

These devices suffer from various drawbacks. Notably, they require users to sit down for a deliberate neurofeedback session, which requires the full attention of the user. Moreover, they do not provide reliable quality in data collection, and are not suited for data collection in various contexts as they are very sensitive to perturbations.

SUMMARY

Firstly, innovations in high-input-impedance amplifiers and high-resolution analog to digital converters has allowed for the reduced cost and size of these electronic components. This change has permit us to construct a portable EEG device which can acquire a brain signal with a comparable accuracy to the large, prohibitively expensive, medical grade systems previously used in clinical settings.

Secondly, a design of the EEG sensors used permits the acquisition of high quality data, despite a variety of ambient noise artefacts. The unique shape of the electrodes permits a signal to be read from the top of the head of the user without the use of conductive liquid or gel. The mechanical integration of the electrode in the headphones allows for a consistent contact with the surface of the user's head, reducing movement artefacts. Electronic pre-amplification, analog filtering and shielding reduce ambient electromagnetic noise.

Thirdly, improved digital signal processing computational algorithms has permit the isolation of valid brain signal amidst the noisy data acquired by the EEG electrodes. The combination of analog driven right leg circuits, analog and digital filtering, digital remontage referencing, and blind source separation algorithms yield a higher quality signal than was previously possible.

Finally, the use of advanced machine learning classification algorithms permits the identification of physical and mental states of the user via the acquired and decomposed EEG signal. Modern statistical information theory signal processing algorithms and non-linear time-frequency transformations allows for the extraction of unique features, which correlate with the desired physical and mental states. Non-linear classifications algorithms use these features to determine the real-time physical and mental state of the user, via identification of feature patterns common to previous users.

According to an embodiment, the low cost, easily accessible over-ear headphones can be applied to provide the ability to measure cognitive states from a consumer EEG device embedded in a headphone, and use this information to give the user feedback in real time on changes in their mental state, in order to condition the user's brain to tend towards the desired state. Moreover, monitoring of brain activity through EEG-enabled headphones permits the user to visualize and interact with their level of concentration in real-time, providing insight and tracking previously unavailable outside of a clinical EEG laboratory. Furthermore, it can be applied to many mental health ailments, including but not limited to attention deficit disorders.

According to an aspect of the invention, there are provided headphones comprising:
earcups to be placed about ears of a user;
a headband linking the earcups and extending above a head of the user;
a flexible band distinct from the headband such as to flex independently therefrom and secured below the headband for contact with the head of the user;
headband electrode sockets formed within the flexible band for receiving headband electrodes, the sockets having an electrically conductive base.

According to an embodiment, the flexible band has a shape at rest not conforming with a head by providing the flexible band with a radius of curvature larger than a radius of curvature of a top area of a human head.

According to an embodiment, the flexible band has a flexibility which makes the flexible band deform under a weight of the earcups to conform with the head of the user.

According to an embodiment, the flexible band has a shape at rest characterized by a radius of curvature between 85 mm and 100 mm, and is made of a resilient material which under the weight of the headphones, which is between 100 g and 1 kg, adopts a radius of curvature between 70 mm and 85 mm.

According to an embodiment, the flexible band is deformable under the weight of the earcups to conform with the head of the user, while the headband does not substantially flex.

According to an embodiment, there are further provided headband electrodes to be embedded in the sockets of the flexible band and having a portion thereof protruding downwardly from the flexible band.

According to an embodiment, the headband electrodes comprise a flexible substrate and a plurality of legs extending therefrom and protruding from the flexible band.

According to an embodiment, the each one of the legs has a length between 4 mm and 9 mm.

According to an embodiment, the flexible substrate is both electrically conductive and flexible such as to allow the legs to change orientation with respect to the flexible substrate.

According to an embodiment, each of the headband electrodes comprises a male connector to fit with a corresponding female connector within the base of a corresponding one of the sockets to hold the headband electrodes in the sockets and form an electrical connection between the legs and the electrically conductive base within the sockets.

According to an embodiment, the headband electrodes are user-detachable from the base without having to dismount the flexible band.

According to an embodiment, the flexible band comprises three headband electrode sockets, one at a center of the flexible band and two others provided more laterally with respect to the one at the center.

According to an embodiment, the two headband electrode sockets provided more laterally each are distant of about between 45 and 70 mm from the headband sensor at the center.

According to an embodiment, there are further provided earcup electrodes on the earcups for contact with a head surface behind an ear of the user, or on a rear surface of the ear of the user.

According to an embodiment, the earcup electrodes comprise conductive fabric.

According to an embodiment, the earcup electrodes comprise an inward earcup electrode provided on an inward surface, where the inward surface is directed toward the rear surface of the ear, on at least one of the earcups.

According to an embodiment, the earcup electrodes comprise an upper rear earcup electrode and a lower rear earcup electrode, respectively located at an upper rear location and a lower rear location on the inward surface of the at least one earcup.

According to an embodiment, the earcup electrodes further comprise an outward earcup electrode provided at an outward surface, where the outward surface is directed toward the head, in a region of the mastoid when the headphones are worn.

According to an embodiment, the base in the headband electrode sockets comprise a biasing element for adjusting a length of protrusion of the headband electrodes downwardly from the flexible band.

According to another aspect of the invention, there are provided headphones comprising:
a headband extending above a head of the user;
a flexible band distinct from the headband and secured below the headband for contact with the head of the user;
removable headband electrodes, to be embedded in sockets formed in the flexible band, and having a portion thereof protruding downwardly from the flexible band.

According to an embodiment, the headband electrodes comprise a flexible substrate and a plurality of legs extending therefrom and protruding from the flexible band.

According to an embodiment, the each one of the legs has a length between 4 mm and 9 mm.

According to an embodiment, the flexible substrate is both electrically conductive and flexible such as to allow the legs to change orientation with respect to the flexible substrate.

According to an embodiment, each of the sockets formed in the flexible band comprises an electrically conductive base for receiving the removable headband electrodes.

According to an embodiment, each of the headband electrodes comprises a male connector to fit with a corresponding female connector within the base of a corresponding one of the sockets to hold the headband electrodes in the sockets and form an electrical connection between the legs and the electrically conductive base within the sockets.

According to an embodiment, the headband electrodes are user-detachable from the base without having to dismount the flexible band.

According to another aspect of the invention, there are provided headphones comprising:
earcups to be placed about ears of a user;
a headband linking the earcups and extending above a head of the user;
a flexible band distinct from the headband and secured below the headband for contact with the head of the user;
headband electrodes embedded in the flexible band;
earcup electrodes on the earcups for contact with a rear surface of an ear of the user.

According to an embodiment, the earcup electrodes comprise conductive fabric.

According to an embodiment, the earcup electrodes for contact with the rear surface of the ear are on an inward surface of the earcup directed toward the rear surface of the ear.

According to an embodiment, the earcup electrodes for contact with the rear surface of the ear comprise an upper rear earcup electrode and a lower rear earcup electrode, respectively located at an upper rear location and a lower rear location on the inward surface of the at least one earcup.

According to an embodiment, there is further provided an outward earcup electrode provided on an outward surface of the earcup directed toward the head, in a region of the mastoid when the headphones are worn.

According to another aspect of the invention, there is provided a method for collecting EEG data, the method comprising: laying onto a head of the user a headband of headphones, the headband linking earcups; contacting with the head of the user a flexible band distinct from the headband and secured below the headband; letting the flexible band adopt a shape of a portion of the head of the user under the weight of the earcups; contacting headband electrodes embedded in the flexible band with a scalp of the user; and collecting data from the headband electrodes.

According to an embodiment, there is further provided collecting data from the earcup electrodes located on a surface of the earcups.

According to an embodiment, there is further provided identifying features in the collected data within time windows of the collected data.

According to an embodiment, there is further provided upon identifying the features, feeding the features to a machine learning classifier to identify patterns in the features.

According to an embodiment, pattern identification comprises determining a state of concentration.

According to an embodiment, there is further provided upon identification of the patterns, feeding the patterns to a meta-classifier to personalize pattern identification.

According to an embodiment, there is further provided upon determining a state of concentration, providing a feedback to the user, the feedback being dependent on the state of concentration as determined.

According to an embodiment, providing the feedback comprises determining a moment when to provide the feedback that is expected to maximize an effect of the feedback to the user.

As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
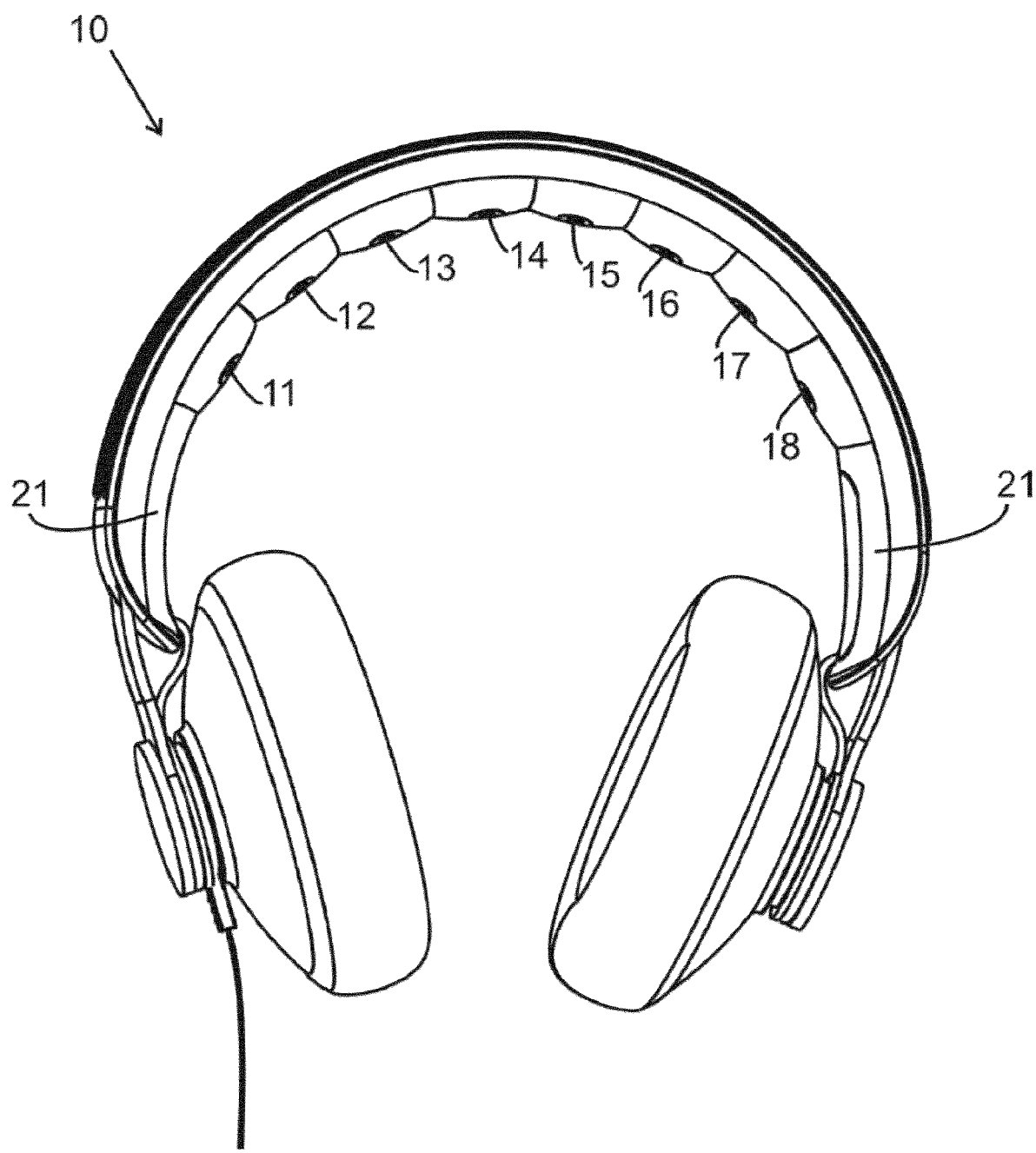
FIG. 1 is a front view illustrating headphones comprising biosensors, according to an embodiment.

Many people who work in stationary and intellectually demanding jobs express that they have difficulty concentrating for extended periods of time. The inability for humans to concentrate for a long time has been well quantified, and is understood to be a severe problem in many work environments. Similarly, many people diagnosed with attention deficit disorder and attention deficit trait express a physiological inability to concentrate for extended periods of time. The rate of diagnosis of attention deficit disorder is increasing, while human performance on sustained attention tasks decreases.

The present invention integrates EEG sensors into over-ear headphones which are both usable as typical headphones, while being adapted for providing a high-quality contact of the sensors with the user's skin for data collection. The EEG sensors can be used to help users monitor, track, and improve attention, alertness, and concentration while they work. Other applications requiring the use of EEG sensors for electrical data collection on a user's head can be implemented using the presently described headphone which comprises sensors with high-quality contact that is well maintained over time.

Applications such as concentration monitoring can be advantageously complemented with feedback reactions, such as those implementing the principle of neurofeedback, or similar feedback, among other features. The pair of over-ear headphones, can output collected data to a computing system implementing machine learning techniques to deliver neurofeedback for improving concentration. Furthermore, while neurofeedback is typically a deliberate task that requires full attention and the help of a trained clinician, the present invention permits neurofeedback to take place in any environment, while the user performs their own work. This permits the user to get the benefits of a neurofeedback-like type of feedback, while working on any task they please. One may thus more accurately refer to this feedback as biofeedback based on a user's cognitive state, and in this sense similar to neurofeedback. Other types of feedback (which are not neurofeedback) can be performed, such as reminding people to get back to task. Any other application requiring the use of EEG sensors for electrical data collection on a user's head can be put into effect while the user is working on a task or moving, since the headphone comprises a flexible band beneath the headband, as well as a particular sensor design, that allows the EEG sensors to make a high-quality contact with the user's scalp that is well maintained over time.

Computational algorithms can be applied to the data extracted from the signals coming from the variety of sensors, including but not limited to EEG, to extract information which can be inputted to a machine learning classifier in order to infer the mental and physical state of the user in real time. Other sensors can include, among others, a heart rate sensor, a galvanic skin response sensor, a body temperature sensor, an accelerometer, a gyroscope, etc.

According to an embodiment, the inferred mental and physical state can be used to allow the user to track, monitor, and improve their attention, alertness, and concentration in real time. One may also monitor features defined as engagement, cognitive workload, executive functioning, sustained attention, mind wandering, distraction, etc. This is accomplished via visual, auditory, and physical feedback to the user of their current physiological state in real-time, based on the principle of biofeedback. This feedback is provided while the user accomplished any desired task, in contrast to the active participation currently required by typical neurofeedback sessions.

The headphones are designed to be used in a primarily stationary setting, although typical movements implied by desk work is permitted, while the user is performing an intellectually stimulating task. The headphones are targeted towards desk workers who wish to improve attention during their workday.

Statistical analysis of the users mental and physical state across time may be provided. This analysis permits quantification the inferred efficacy of their workflow, monitoring of stress and engagement levels, changes, and improvements over time.

Suggested habit changes may be given to the user based on the historical trend of their inferred mental and physical state. These suggestions may be given in real-time in the form of feedback, or in aggregate before or after a session. The effect of changes in the user's habits in response to suggestions, feedback, changes in workflow, and changes in music played by the headphones may be used to modify the predictions and suggestions given.

Integration with wearable devices, software programs, and other monitoring tools may allow for more customized and relevant feedback. The aggregation of several input sources, i.e., biosignals, which are electrical data collected from biosensors on the body, may be used to improve the accuracy of the prediction algorithms used to infer the mental and physical state of the user. The user experience, including but not limited to the current music and the feedback given, may change as a function of the task being performed by the user. User-specific preferences may be used to customize the experience delivered by the present invention, through modification of the audio, visual, and physical feedback delivered.

FIG. 1 illustrates a first embodiment of the headphone. Another embodiment will be described further below in relation with FIGS. 5A-5G. Some features described in relation with FIG. 1 should not be viewed as exclusive to the embodiment of FIG. 1 as they can also be applied to the other embodiment described in relation with FIGS. 5A-5G.

Figure 2:
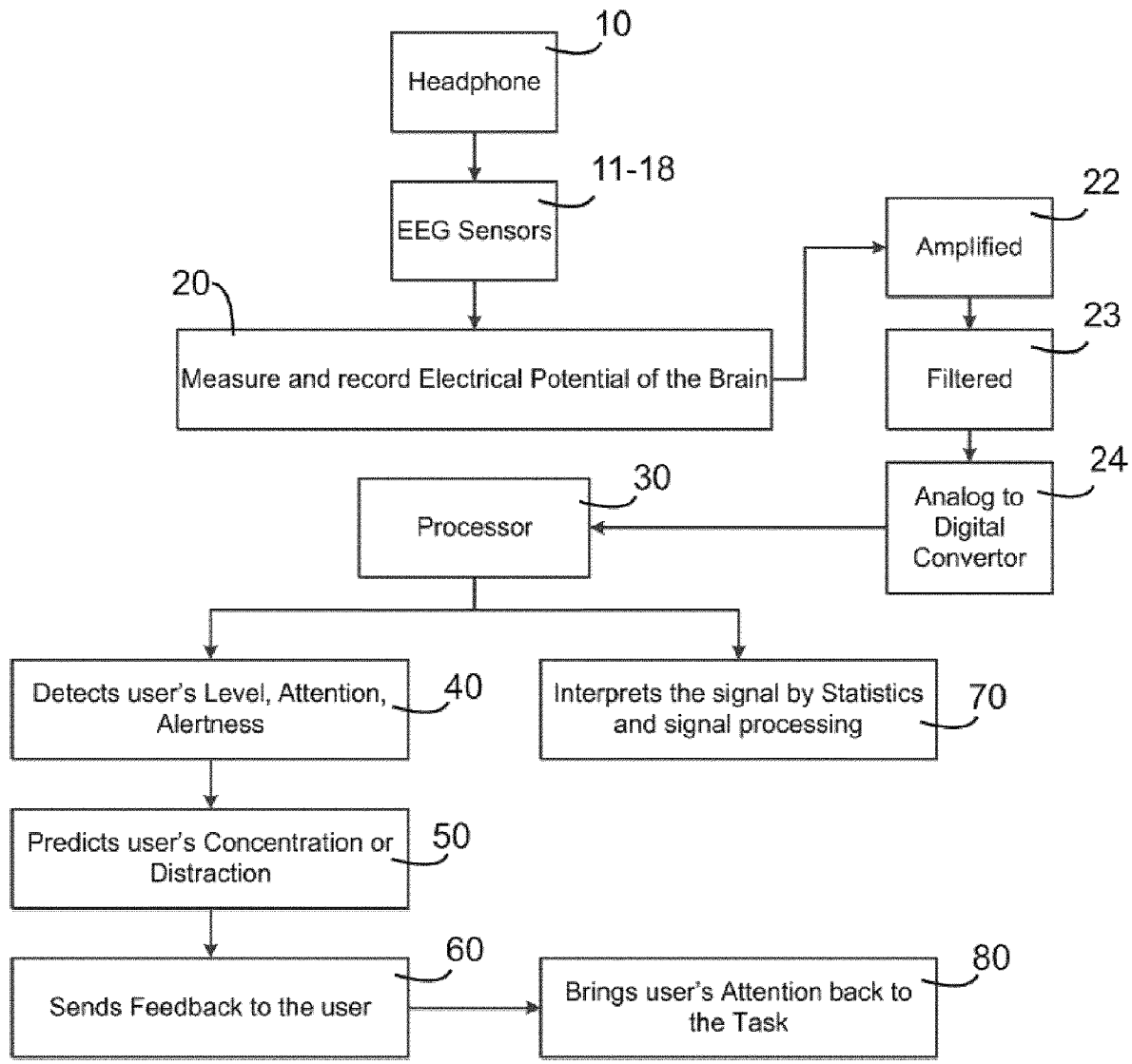
FIG. 2 is a schematic diagram illustrating the use of headphones having sensors to provide feedback for concentration, according to an embodiment.

As shown in FIGS. 1-2, the headphone 10 uses a plurality of electroencephalographic and biopotential sensors 11-18 to measure and record electrical potentials originating in the brain. Electrical potentials originating from other sources in the body, such as the heart, the eyes, or muscles, can be measuring by providing sensors at the appropriate locations on the surface of the body. In this case, where electrical potentials originating from the brain are the primary source of data, the sensor electrodes 11-18 are embedded in an upper band 21 of the headphone 10, measuring voltage on the scalp 20. This information is processed and relayed to a computer 30, which interprets the signals to determine the current state of the brain 40. Among other states, the computer detects the user's level of attention and alertness 40, which are used to predict the user's concentration or distraction 50 with respect to their given task.

The voltage measured by the electrodes 11-18 is amplified 22, filtered 23, and passed through an analog-to-digital converter 24. According to an embodiment, the signal is then transferred to the computer 30 via Bluetooth, Wi-Fi, or a similar protocol. In the computer 30, the signal is pre-processed in order to remove noise 90. Several features can then be calculated from the signal, using a variety of statistics and signal processing techniques 70.

According to an embodiment, this information is fed into a machine-learning model, which predicts the state of concentration of the user 50. This prediction can be used to send feedback to the user 60 of their state of concentration in real-time. The mental state of the user will be actively influenced (based on alarms, reports, etc.) or passively influenced (by subtly changing volume of the music played by the headphone) by this feedback, improving their concentration over time.

Figure 3:
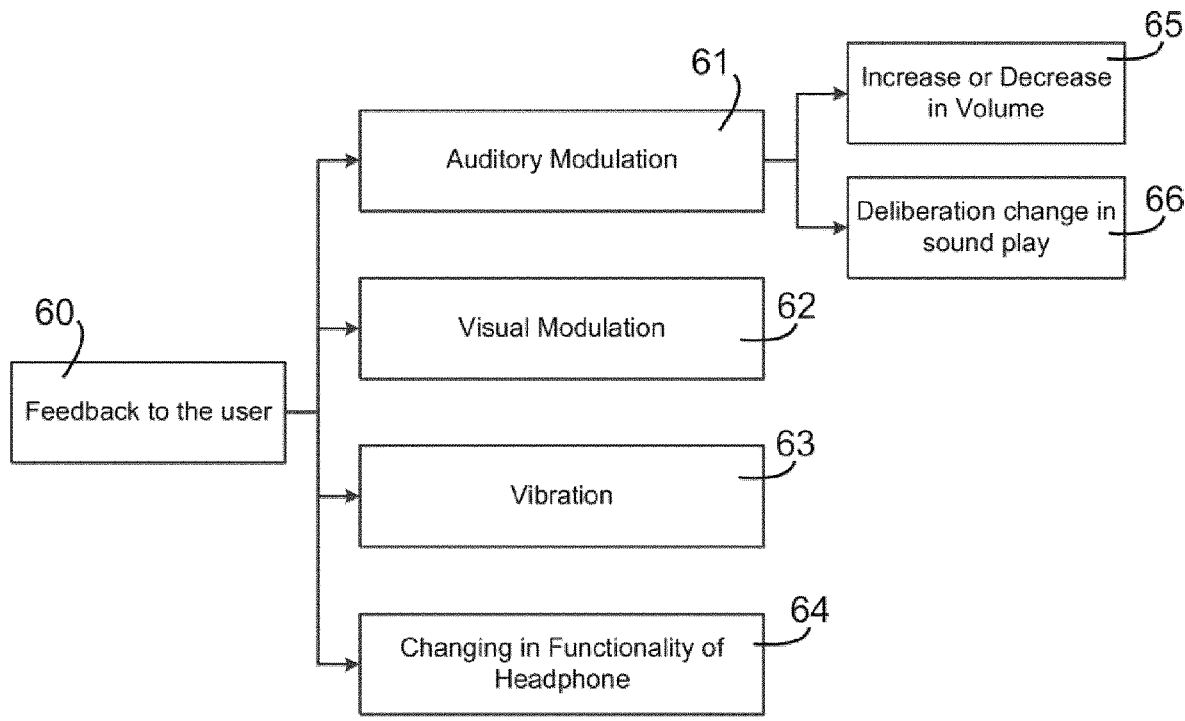
FIG. 3 is a schematic diagram illustrating feedback to the user, according to an embodiment.

As shown in FIG. 3, the feedback 60 described above will be delivered in the form of a distinguishable notification, the purpose of which is to alert the user of their changed mental state and bring the user's attention back to their task. This will be in the form of an auditory modulation 61—an increase or decrease in the volume 611, or a deliberate change in the sound played through the headphones 612. Visual feedback 62 on a computer, mobile device, or integrated light may also be delivered, via modulation of the visuals 62 on the screen. Other forms of feedback include vibration 63, or changes in the functionality of certain headphone features 64 (changing noise cancelling, or turning on/off notifications) or other similar application-level changes. Several forms of feedback may be combined, in order to change the user experience. The feedback may vary in style, intensity, and frequency depending on a variety of user and setting-specific features.

Figure 4:
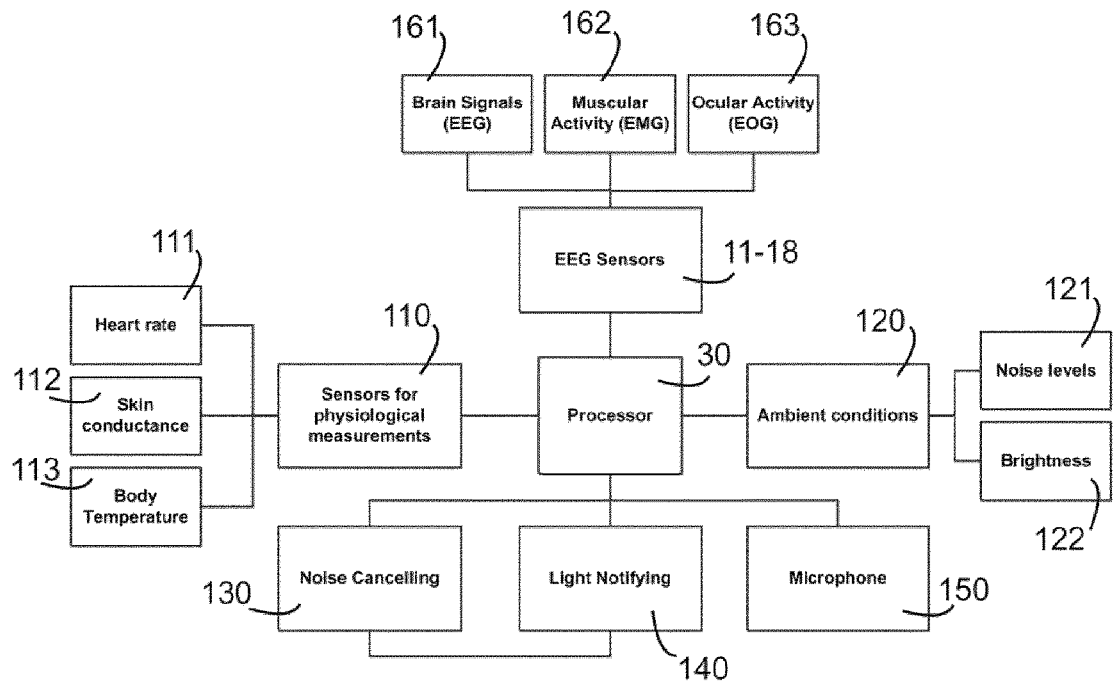
FIG. 4 is a schematic diagram illustrating an architecture of headphones having a plurality of different sensors, according to an embodiment.
Figure 5A:
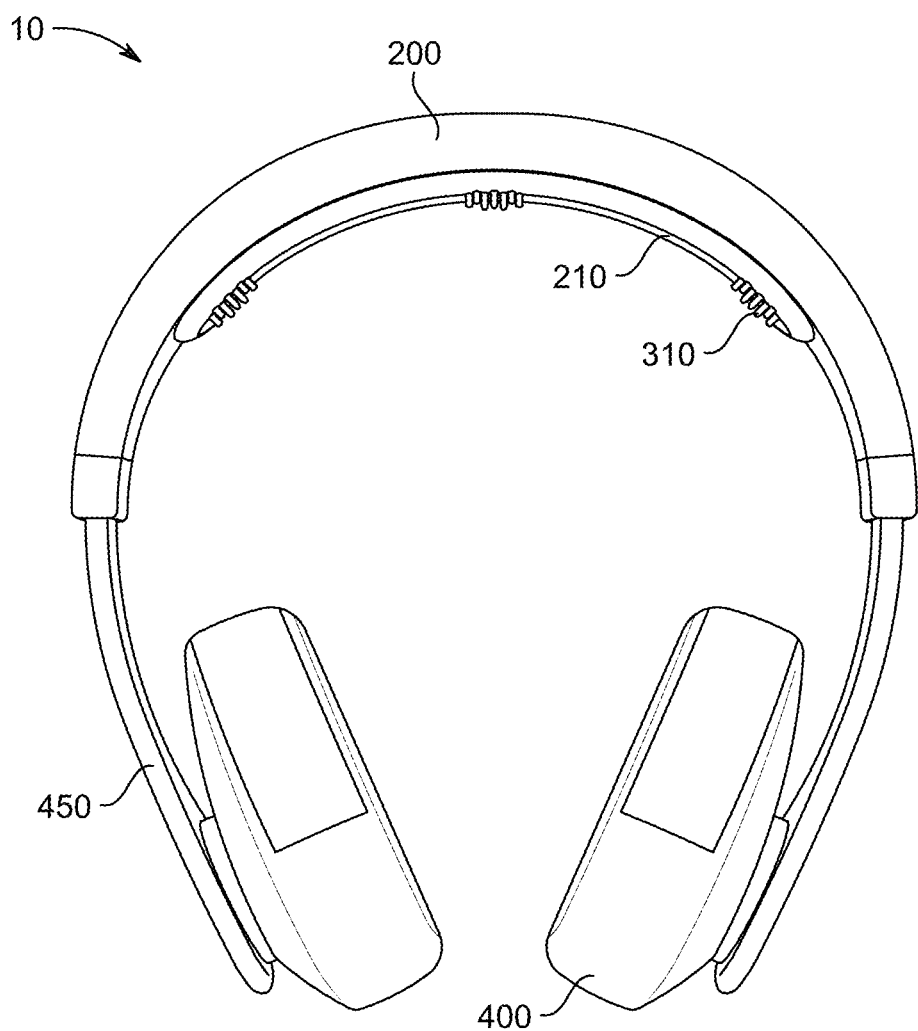
FIGS. 5A-5G are a front view, a first side view, a second side view, a bottom perspective view, a bottom view, a side perspective view and a top view, respectively, illustrating headphones having EEG sensors, according to an embodiment.
Figures 5B, 5C:
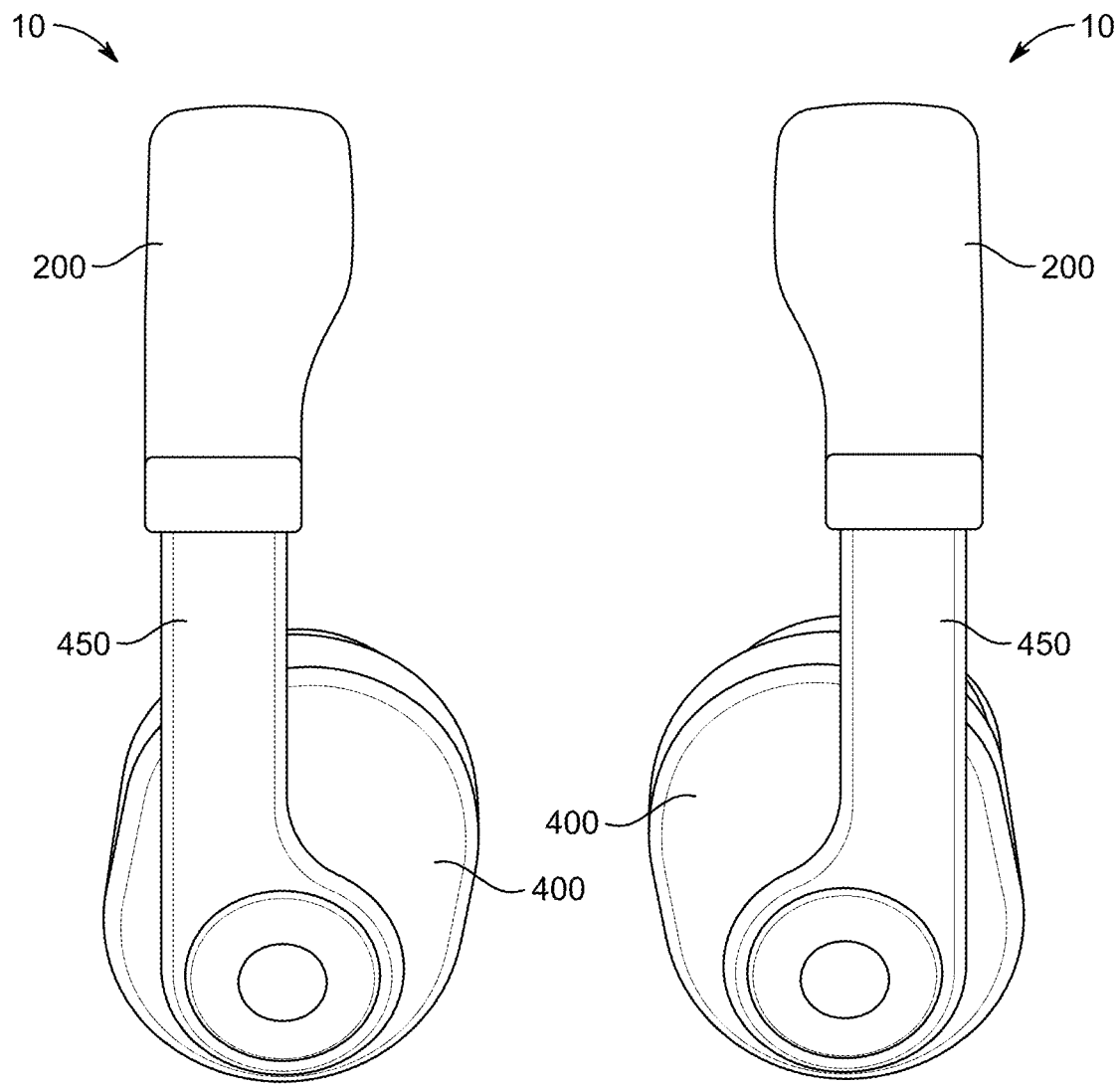
Figure 5D:
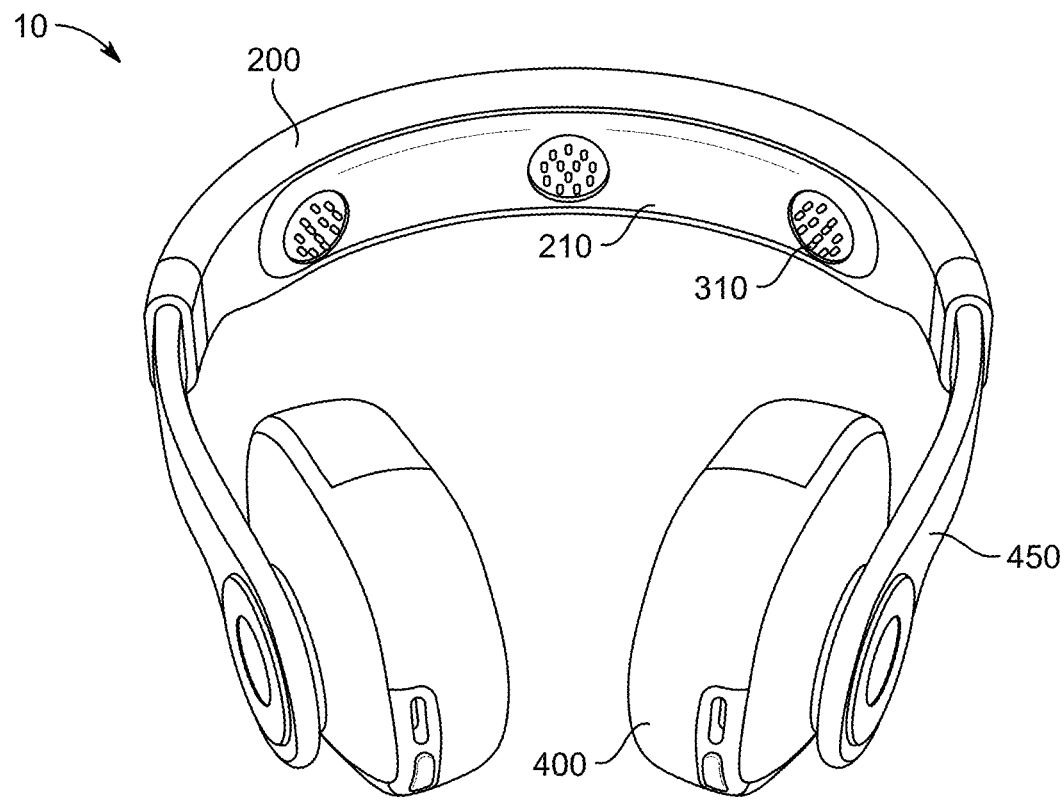
Figure 5E:
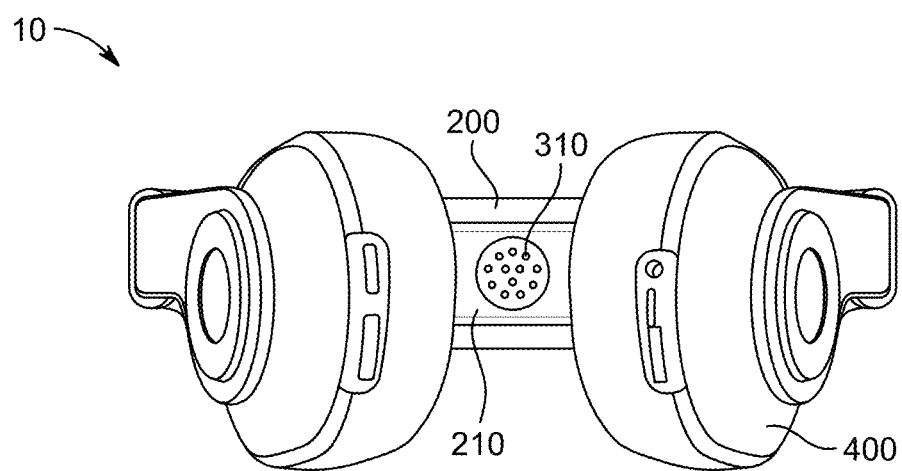
Figure 5F:
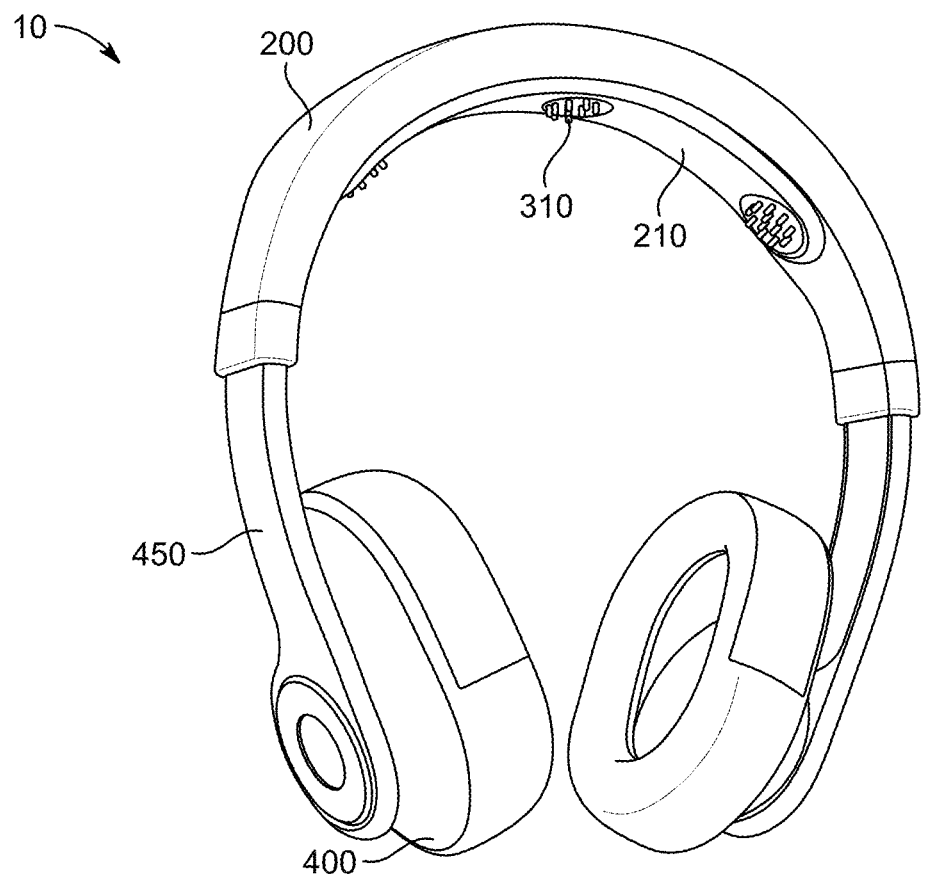
Figure 5G:
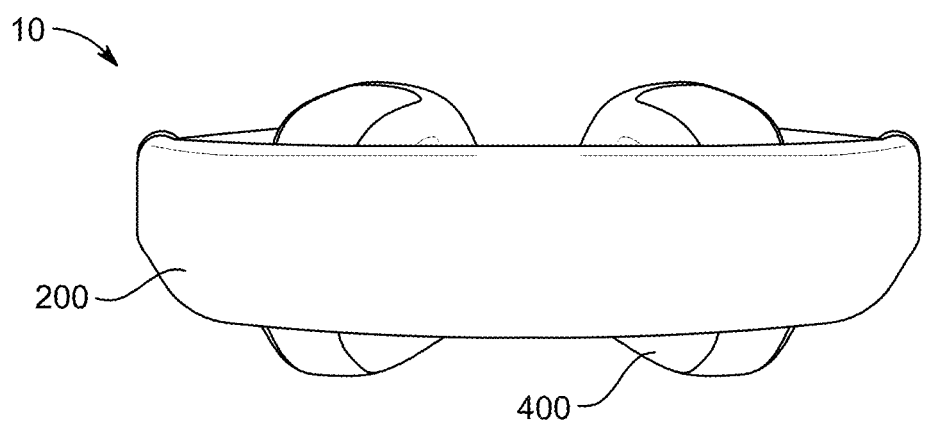

As shown in FIG. 4, additional sensors embedded in the headphones to detect a variety of physiological measurements 110 including heart rate 111, skin conductance 112, and body temperature 113. Ambient conditions 120 such as noise levels 121 and ambient brightness 122 are also recorded. The computer 30 uses these measurements in addition to the brain activity when predicting attention and alertness, as well as when determining whether to send feedback. The individual combination of sensors and algorithms used in the determination of the user's mental state and in the delivery of feedback will be customized to the user's personal physiology, preferences, daily patterns, and response to previously given feedback.

Again, as shown in FIG. 4, the system comprises of electrodes 11-18, of passive or active nature, whereas active pertains to the proximity of an amplifier to the source of the signal. The electrodes 11-18 should be dry electrodes, which are better suited for use with headphones. The electrodes 11-18 will record brain signals (EEG) 161, muscular activity (EMG) 162, ocular activity (EOG) 163, heart activity (ECG), or any combination of the above.

The headphones 10 may also incorporate noise-cancelling 130—either passive or active—in order to change and improve the user's work environment. An activity light notifying 140 surrounding people that the user is currently busy may be included, in order to prevent disturbances during desired times. In addition, the headphones may incorporate one or several microphones 150, which may be used by the user to record and communicate, while also being used to monitor the external noise level providing insight for better noise cancelling and prediction of concentration.

The headphones 10 are anticipated to be used in a work environment, in order to reduce distraction and improve productivity during a task. The user will be able to customize the feedback experience to the work currently being done. Personal profiles, modulated as a function of the user's preferences and needs, will allow for a catered experience as a function of the desired state.

Using a similar methodology, several other mental or physical states may be predicted via classification of the combination of signals acquired from the headphone's sensors. These may include but are not limited to stress, sadness, anger, hunger, or tiredness. Likewise, the presence of neurological disorders such as epilepsy, anxiety disorder, and attention deficit disorder may be predicted in a similar fashion.

The system may modify human behavior through the delivery of brain-state inspired feedback. These modifications will yield short-term changes in behavior through immediate user response to the feedback provided. An example of this is returning attention to the desired task when notified of the current state of distraction. These modifications can also induce long-term neurophysiological changes due to the user's subconscious response to the feedback provided. An example of this is a subconscious conditioning of the neurological sustained attention system, improving the ability to sustain focus for long durations.

Trends and analytics performed on the recorded bio-signal data provide information on the user's mental and physical state, and allow for prediction of user behavior and their optimal states.

The system uses a combination of one or more sensors to measure bio-signals and ambient conditions, in order to measure and infer the mental and physical state of the user. These sensors include but are not limited to electrodes, temperature probes, accelerometers, pulse oximeters, microphones, and pressure transducers.

The shape and structure of the electrodes are such that they have the capability of passing through the hair and making direct contact with the skin. Examples or embodiments are legged sensors, comb-like structures, flat plates, peg arrays and spring-loaded pegs. The shape and material choice ensure a consistent contact with the skin, minimizing connection impedance.

The system may include a microphone that monitors external ambient noise. This information may be used to modulate the feedback, the music, or the noise cancellation as a function of the level of environmental distraction predicted from the measured ambient conditions. The ambient sound may integrate with the sensor data in order to provide more accurate prediction of the user's mental and physical state. Customizable preferences, including but not limited to the choice of music played through the headphones, may be modulated as a function of the environmental noise. White noise, binaural beats, instrumental music, or user-defined preferences may be used alone or in combination in order to create an ideal work environment for the user. Changes in predicted concentration as a function of the music played may be used to improve focus prediction and feedback delivered.

The system may include passive or active noise isolation. High-density foams, leather, and other materials may be placed around the ear cup in order to isolate the user from external environmental noise. Ambient sound monitoring via the microphone may be used to determine which sounds should be attenuated and which should be amplified.

Body temperature fluctuations may be monitored, and used to improve prediction of the user's mental and physical state. Body temperature may be used to detect long-term trends in user productivity, related to circadian rhythms, energy levels, and alertness. This information may be used to improve the feedback delivered to the user.

Recording of heart rate can provide additional information on body states, including attention and stress levels. Pulse oximetry, balistocardiogram, electrocardiogram, or other substitutable technology may be used for measuring heart rate near the ear or scalp. Analytics performed on heart rate measurements may be used to infer physiological characteristics, including but not limited to heart rate variability, R-R distance, and blood flow volume. These computed physiological characteristics may be used to modulate the feedback delivered to the user, in the form of delivering suggestions for improving concentration.

The system may include sensors in the ear cup, touching the ears or in the area around the ears, for the purpose of recording bio-signals.

The system may include a mechanism for preventing unwanted mechanical movement of the headphones with respect to the head. A possible embodiment of this mechanism is a pad which contacts with the user's head and locks onto the bone structure of the skull, preventing motion of the headphones with respect to the scalp. This mechanism may also be used to promote positioning repeatability of the headphones and sensors on the head.

According to an embodiment, each electrode is embedded in a stabilizing mechanical structure, designed to reduce cable movement, external electrical noise and electrical contact breaks. The stabilizing structure keeps the electrodes in consistent contact with the surface of the user's head during movement.

According to an embodiment, the system comprises an adjustment mechanism, allowing the user to better position the headphones on their head. The mechanism may allow for radial adjustment of the shape of the headphones, adapting for variations in users' head width. The mechanism may allow for adjustable vertical positioning of the sensors, in order to evenly distribute the downward force and ensure proper contact of the electrodes.

Where the system interfaces with the side of the head, leather, fabric, or memory foam may be used for comfort. The material contact interface may be tuned in order to prevent movement of the headphones with respect to the user's head, as well as to dampen vibrations.

Electrodes along the top band may be static, or attached to a moving mechanism that allows the electrodes to retreat completely into the band when not in use. The movement of the electrodes may be controlled via a manually actuated interface, or automatically via the placement of the headphones on the user's head. According to an embodiment, the electrodes are removable, at which point the biosensor headphone becomes a normal headphone. For example, the electrodes can be made removable using a snap-fit connector, or a connector with a male portion engaged in a female portion and held therein with frictional forces.

The system may include a rotational mechanism along the axis connecting the user's ears, allowing the top band to be rotated to contact the forehead, the back of the head, the neck, or other parts of the scalp. This would permit positioning the sensors at other key locations on the head to perform data collection from the prefrontal cortex, the parietal lobe, the occipital lobe, or the neck, for example.

According to an embodiment, the system has the capability of playing an external audio stream over-the-air from a computer or mobile device while simultaneously transferring signals recorded from the headphones to said device. The data-transfer protocol may take place via Bluetooth, Wi-Fi, RF-wave, or other similar wireless protocols.

The system may have an activity light that responds to current brain states. This light notifies other parties of the user's current mental or physical state. One such use is to notify nearby parties that the user is currently busy or concentrated, so as to prevent disturbances.

An alternative embodiment may include the use of this technology as an add-on to existing headphones, connecting to the top band of the headphones and functioning independently of the headphones. An alternative embodiment may also include a multi-purpose band that may be used around the neck, arm, head, leg, or other body part.

The system shall be classified as a computer or computational device, for it not only plays music, but has the capability of recording vital signs and bio-potentials, processing them, and generating an output, independently of whether it is connected to a computer or phone device.

Now referring to FIGS. 5A-5G, there is shown an embodiment of the headphone 10 according to various views. The embodiment of the headphone 10 of FIGS. 5A-5G comprises a particular design of headband electrodes 310, embedded in a flexible band parallel but distinct from the headband, and earcup electrodes 360. Other features, such as music, noise-canceling, microphones, other sensors and add-on features of the headphones described above in relation with FIGS. 1-4, as well as feedback features, are also applicable to the embodiment of the headphone 10 of FIGS. 5A-5G and will not be repeated.

According to this exemplary embodiment, the headband 200 has a flexible band 210 secured thereto and in which is embedded at least one EEG sensor, or biosensor, i.e., a sensor or electrode measuring electrical activity on the body. According to a preferred embodiment, there are embedded three EEG sensors, or biosensors, in the flexible band 210. Additional EEG sensors can be provided on the earcups 400, e.g., by making a portion of the foam forming the earcup 400 conductive.

As discussed above, typical headbands from usual headphones are not designed to bear EEG sensors. As a result, simply integrating EEG sensors to an existing headphone of a given shape is not likely to offer interesting results in terms of electrical contact between the EEG sensors located thereon and the skin on the person's head, i.e., the scalp.

The embodiment shown in FIGS. 5A-5G addresses the issue of suboptimal contact between headphone-mounted EEG sensors and the scalp by providing the EEG sensors on a flexible band distinct (i.e., separate) from the headband and secured to the headband. The flexible band is provided below the headband and is made of a material that renders such band flexible up to the point that the flexible band generally adopts the shape of the head of the user while taking into account that the EEG sensors protrude from the flexible band toward the scalp.

Figure 6:
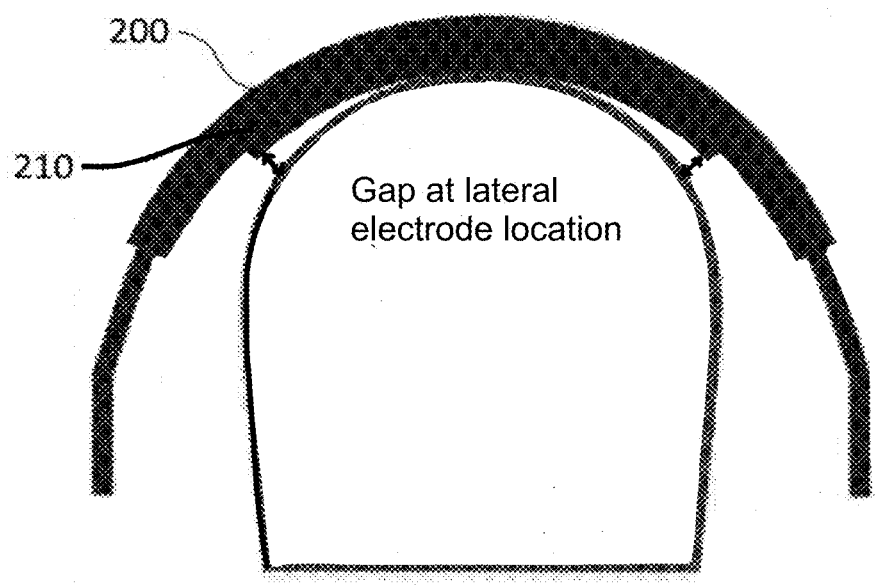
FIG. 6 is a diagram illustrating spacing between lateral electrodes on headphones and the head of a user, according to an embodiment.

The issue of having a headphone set not conforming the user's head is shown in FIG. 6. Getting sufficient signals from electrical activity in the brain requires placing electrodes at different locations on the person's head, and not only at the top of the head. In other words, electrodes need to be placed at locations away from the top center of the head, i.e., at more lateral locations on the head as shown in FIG. 6. This requirement for electrode placement at more than one location including locations away from the top center (while being within the reach of the headband) creates a strict requirement on the headband shape if one wants to achieve high signal quality and reliability from the sensors at these locations. According to an embodiment, the lateral sensors are distant from the center sensor from about 65 mm (i.e., half the head arc length of a standard person), or between 60 mm and 70 mm, or between 45 mm and 70 mm, or between 45 mm and 80 mm. These distances allow electrodes to lie at the C3 and C4 locations according to the international 10/20 standard.

Prior art headphones with sensors failed to achieve high signal quality and reliability from the sensors at locations away from the top center. Typical headbands for headphones were used for these applications, meaning that the purpose of the headband was solely to mechanically link and electrically connect the earcups, while offering a support, preferably a comfortable one, when being laid on the user's head.

However, as discussed above, the purpose of the headband of the present invention, in addition to those of the prior art, is to provide a structure on which the sensors are mounted. These sensors need to be adequately located, maintained at their intended location, and put into contact with the scalp while having a proper contact (to have a high-quality signal) that is maintained over time (so the signal is reliable enough for eventually extract information therefrom).

Moreover, in addition to the main portion of the headband 200, there is provided a flexible band 210, which extends in a shape substantially like a central portion of the headband and is secured under the headband 200 to conform with the user's head when being deformed under the weight of the headphones 10 when being worn.

Each of the headband electrodes is secured at a bottom of the flexible band 210, or lower headband. The flexible band 210 serves the purpose of adjusting the position of each electrode when the headphones are being worn, such that a contact is maintained with the user's head independently of the position of the headband.

Figure 7:
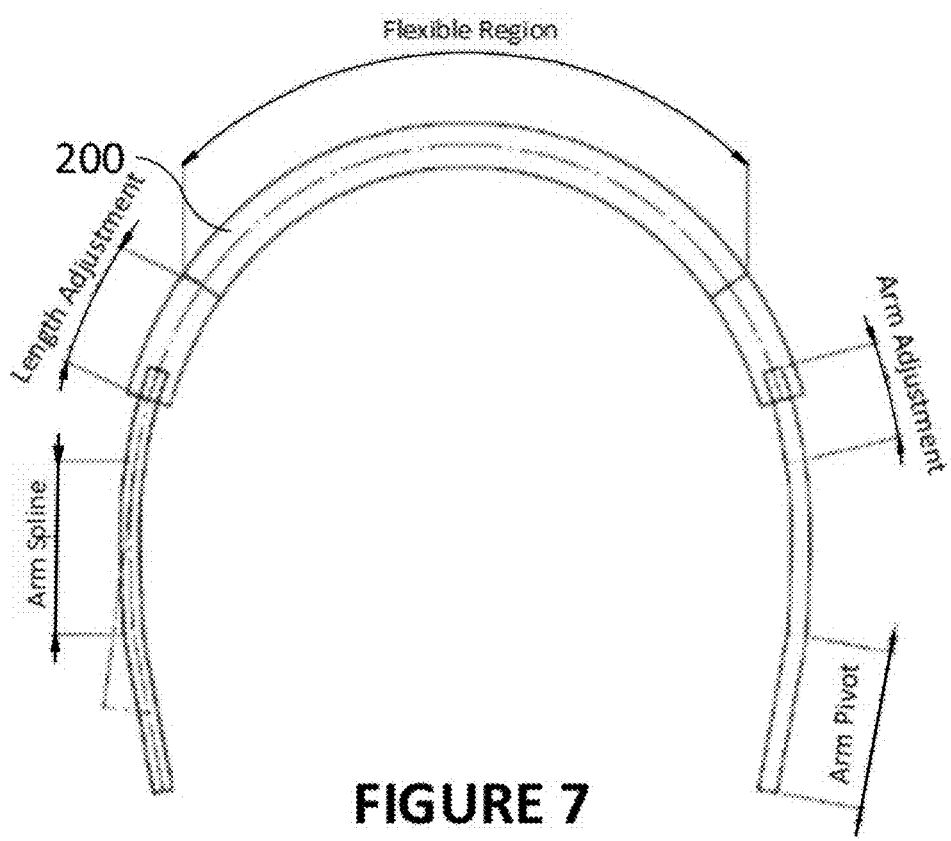
FIG. 7 is a diagram illustrating a headband of headphones, according to an embodiment.

This is done by providing the flexible band 210 with a shape and a material having a flexibility which ensure that upon laying the headband on the user's head, the weight of the headband with the earcups at both ends pushes the flexible band 210 along the surface of the head, including for areas away from the top center of the head, as shown in FIG. 7. However, the flexible band 210 should keep a rounded shape at rest and in use and simply bend or flex when being used, as it should still have some rigidity (although it should be less rigid or stiff than the upper headband 200). It means that the flexible band 210 should not be confused with a fabric or an elastic band, which would have some drawbacks. Notably, if the flexible band 210 was a fabric or an elastic band, it would not provide proper support for the electrodes, it would not allow them to be easily removable with a snap-fit connector, it would be fragile (i.e., easy to tear), it could expose the inner parts such as cabling, and thus it would not be suited for a consumer product.

Figure 8:
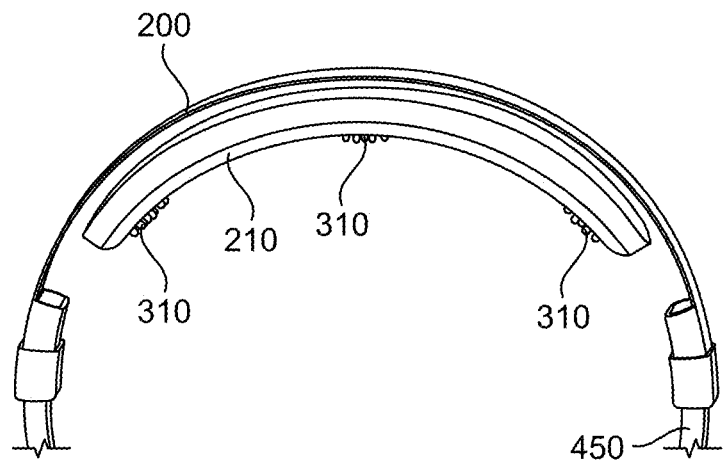
FIG. 8 is a front view illustrating a headband of headphones comprises a lower headband or flexible band, according to an embodiment.
Figure 9A:
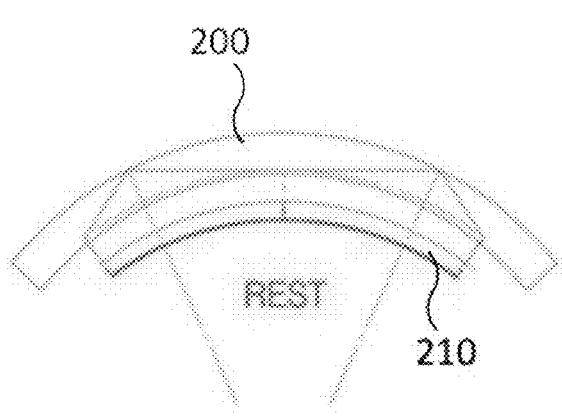
FIGS. 9A-9B are diagrams illustrating the flexible band at rest and independently deformed when being worn, according to an embodiment.
Figure 9B:
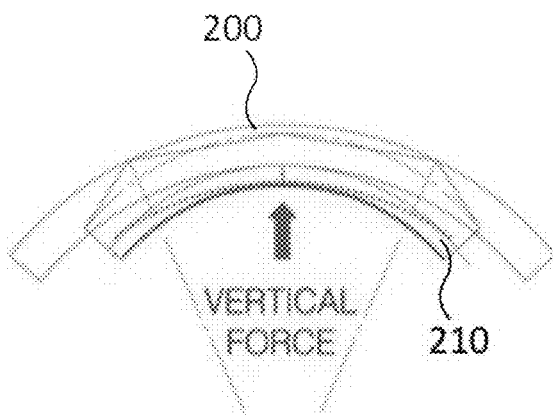

The flexible band 210 is shown in FIG. 8 as being separate from the headband main structure and extending under it. The flexible band is made of any material flexible enough to deform under the weight of the headphone. There are for example many plastics that can deform when a weight corresponding to a few hundred grams is applied on the object. The force is applied by having the central portion of the flexible band 210 applied on the top center of the head and conform therewith, while the lateral portion of the flexible band 210 do not touch the head. If there is no gravity, the flexible band would be at rest, as shown in FIG. 9A, and remain in this position. However, when the headphones 10 are being worn, and as shown in FIG. 9B, the gravity pulls down the sides of the flexible band 210 (those closer to the earcups and originally not in contact with the head). These sides of the flexible band 210 are those deformed by gravity and brought down along the surface of the head, to which they conform, at least approximately. The use of a flexible band 210, which has greater flexibility than prior art head bands, and which is closer to the surface of the head, allows a closer and more conforming contact between the flexible band 210 and the head of the user for locations that are more lateral compared to the top center of the head.

The flexible band 210 thus better conforms to the shape of the head than prior art headbands. Electrodes are thus provided in the flexible band 210 and protrude downwardly from the flexible band to reach the scalp of the user. As discussed further below, additional sensors can be placed on or in the earcups. However, the flexible band 210 comprises the sensors that aim at touching the scalp.

According to an embodiment, there are three sensors, one being located at a center of the flexible band 210 in order to be located on the top center of the user head, and two other lateral sensors located away from the center of the flexible band 210, preferably symmetrically from the center, in order to reach lateral locations on the head as discussed above (those for which the presence of the flexible band 210 ensures better and longer-maintained contact). This is shown in FIGS. 5A-5G.

Figure 10:
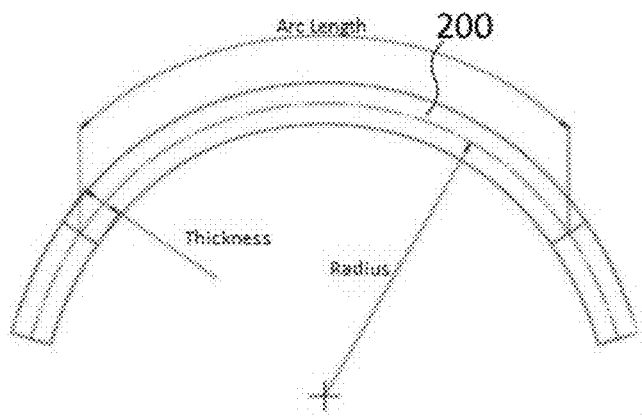
FIG. 10 is a diagram illustrating a flexible band of headphones, according to an embodiment.

Now referring to FIG. 10, the headband 200, or upper headband, can be sized to ensure that when deformed (along with the flexible band 210 underneath) under the weight of the headphones 10, the headband 200 (along with the flexible band 210 underneath) substantially adopts the shape of the surface of the head on which it lies.

Figure 11:
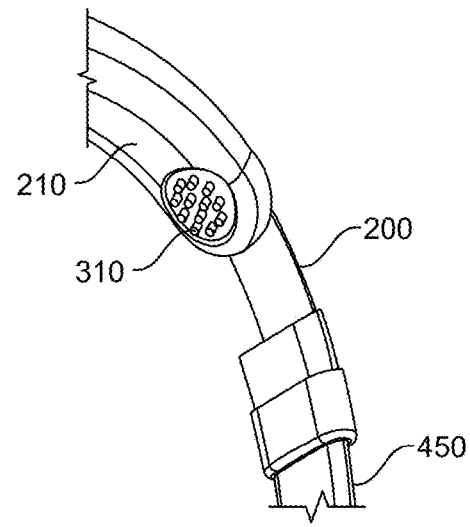
FIG. 11 is a close-up perspective view illustrating a limit of movement of armbands to avoid impacting the flexible band of headphones, according to an embodiment.

Now referring to FIG. 11, there are shown lines that illustrate the maximum position of the earcups holders along the headband. Indeed, a stopper needs to be provided by the sliding rail in which the earcups holders are provided to ensure that the earcups holders cannot be retracted along the headband 200 up to a point where they would hit the flexible band 210 and damage it.

Figure 12:
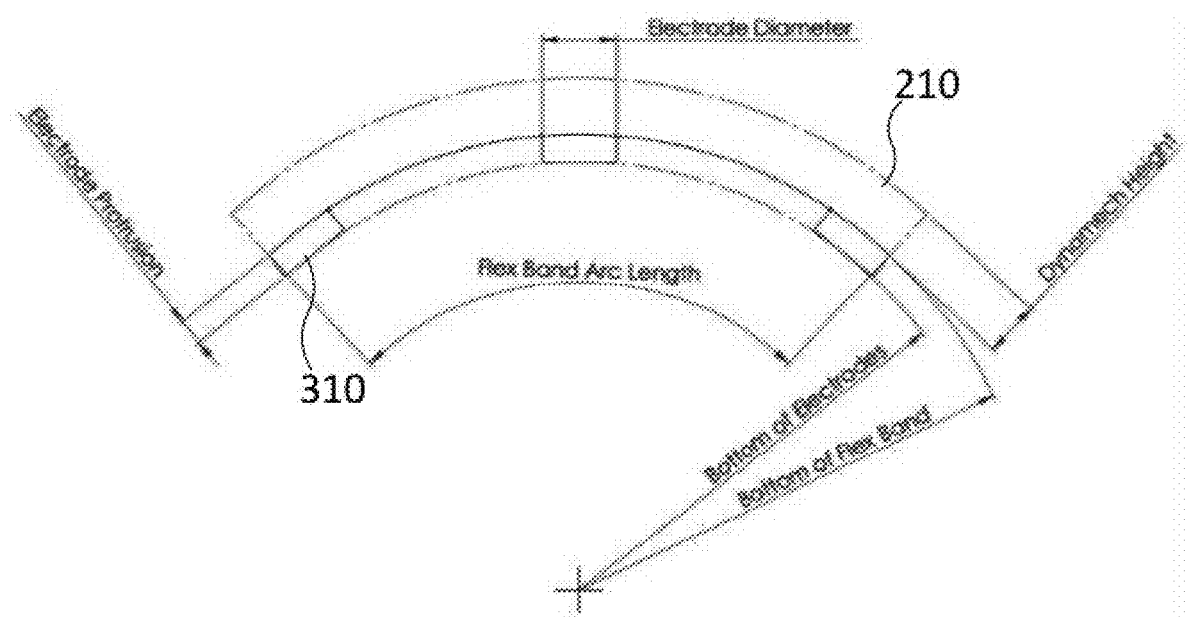
FIG. 12 is a diagram illustrating a flexible band of headphones with electrodes protruding therefrom, according to an embodiment.
Figure 13A:
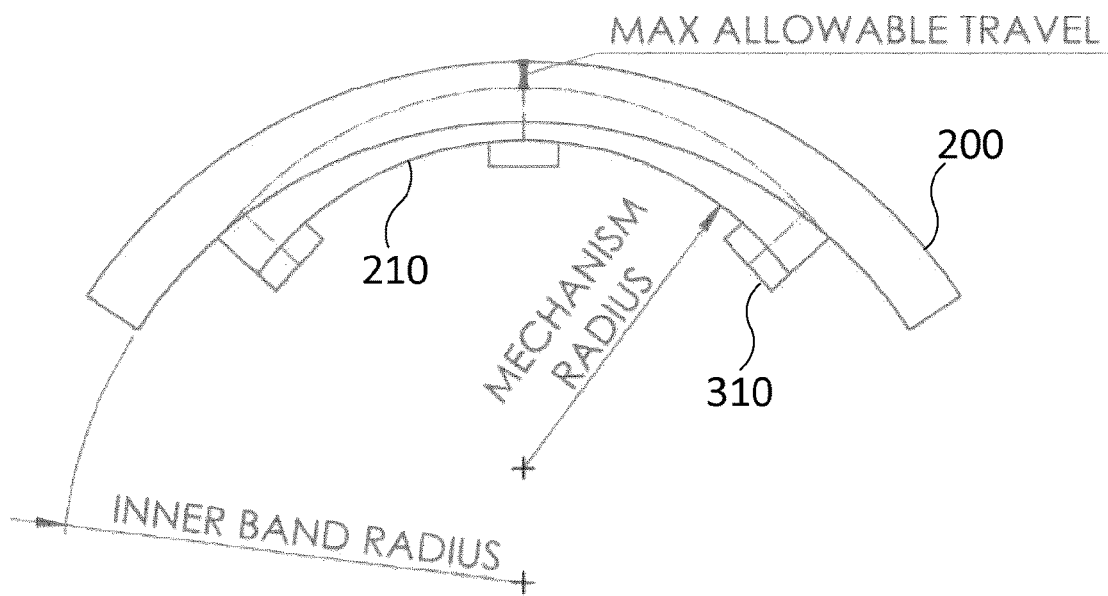
FIGS. 13A-13D are diagrams illustrating a deformation of the flexible band of headphones, according to an embodiment.
Figure 13B:
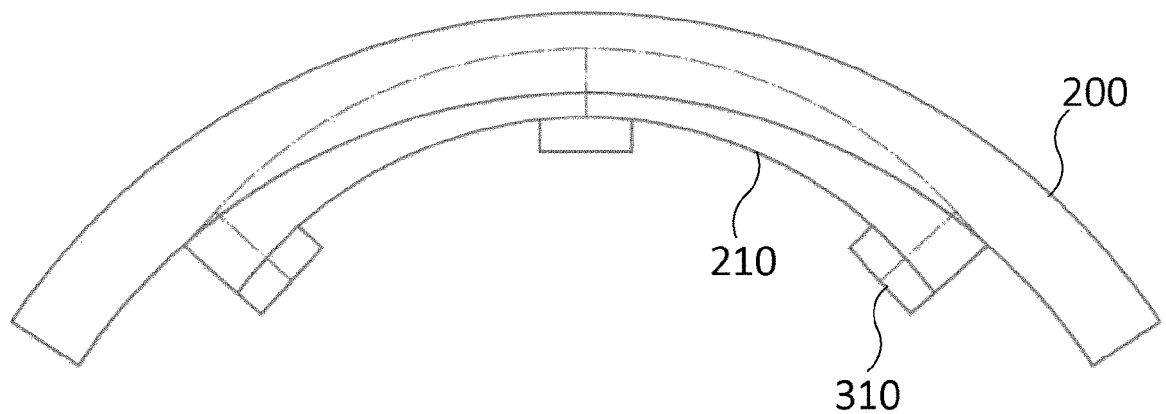
Figure 13C:
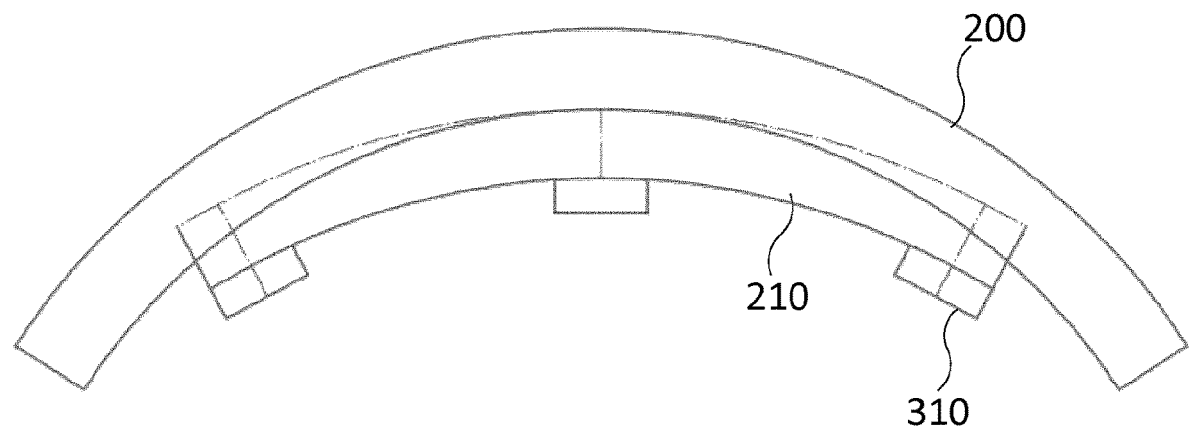
Figure 13D:
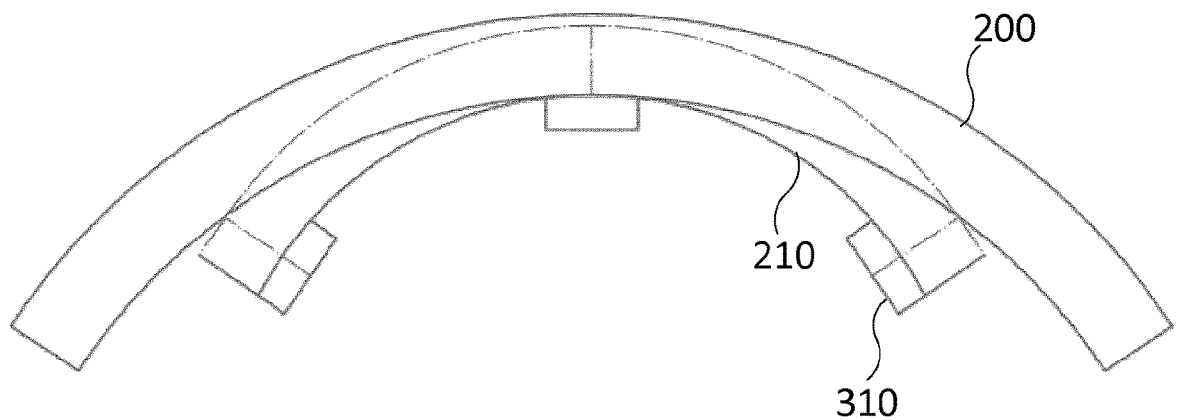

Now referring to FIG. 12, the flexible band 210 can be sized to ensure that when deformed under the weight of the headphones 10, the flexible band 210 substantially adopts the shape of the surface of the head on which it lies, and has its electrodes protrude at a protruding distance which is consistent with standard hair thickness and is not too short such as to prevent contact with the scalp, or too long which would put all the weight pressure into the legs of the electrodes and thus be uncomfortable. According to an exemplary embodiment, the flexible band 210 has a thickness of about 14 mm, or between 12 mm and 16 mm, or between 10 mm and 18 mm. According to an exemplary embodiment, the flexible band 210 has an arc length of about 196 mm, or between 192 mm and 200 mm, or between 180 mm and 212 mm.

The flexible band 210 is flexible in that it can adopt a variety of radiuses of curvature. The upper headband 200 is more rigid and preferably has a larger radius of curvature, but its radius can change too under the application of forces. According to an exemplary embodiment, the radius of the upper headband 200 can vary from a minimum of about 107 mm to a maximum radius about 136 mm. Other variations and ranges are possible, for example the minimum radius can be in the order of 80 mm to 110 mm, and the maximum radius of curvature can be in the order of 120 mm to 160 mm.

At rest, the flexible band 210 should have a radius of curvature chosen between 80 mm and 100 mm, or preferably between 85 mm and 100 mm, or more preferably between 85 mm and 97 mm, so that the flexible band 210 has a radius of curvature larger than that of most human heads (e.g., 80 percentile), measured at their top area, so as to not conform with a user's head when at rest. Upon being laid on the user's head, the weight of the earcups 400, combined to the force of the top of the end on which the flexible band 210 presses, will force the flexible band to deform. Since it is distinct from the upper headband 200 (although they can look to be together by being housed with an envelope or a protecting fabric), the flexible band will deform so as to conform with the head of the user, thereby adopting a radius of curvature below 85 mm, and preferably below 80 mm, but above 70 mm, as allowed by the resilient material forming the flexible band 210 under the effect of the weight of the headphones (most of it from the earcups and arms) which weights a few hundred grams (realistically above 100 g and below 1 kg, and more realistically between 150 g and 500 g, and probably between 200 g and 400 g, more probably about 300 g).

Now referring to FIG. 13A-13D, there are shown measurements of the deformations undergone by the flexible band 210 in relation with the discussion above regarding the radiuses of curvature. It is shown that the flexible band 210, or lower headband, bends independently from the upper headband 200. The flexible band 210 should be larger than most heads at rest. When laid on a head, the weight of the earcups 400 pulls down the ends of the flexible band, which transitions from a large radius of curvature to a small radius of curvature, where the large and small radiuses were discussed above.

Figure 14A:
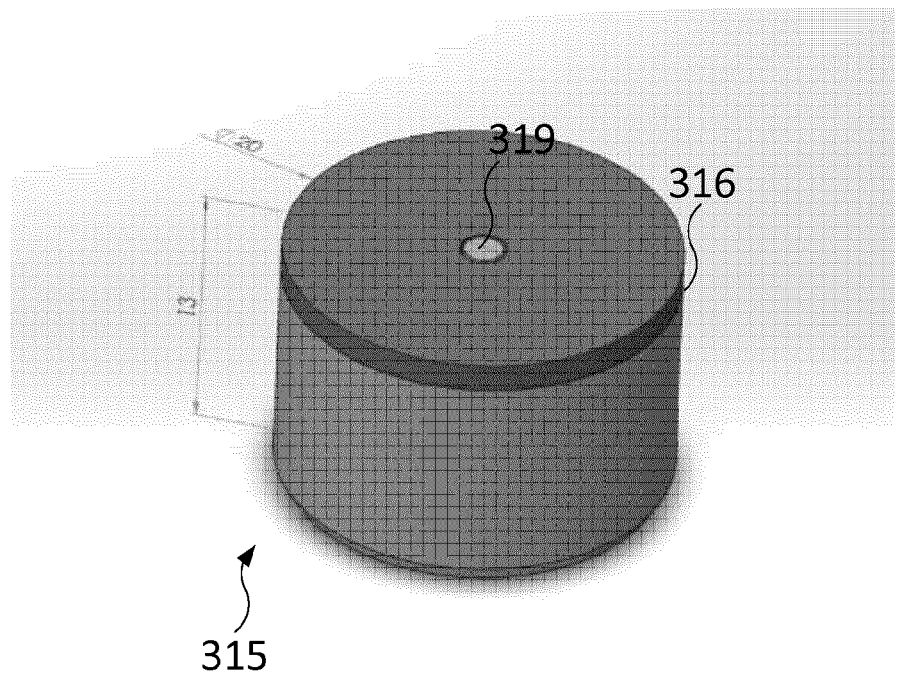
FIGS. 14A-14B are perspective views illustrating a base for the headband electrodes, according to an embodiment.
Figure 14B:
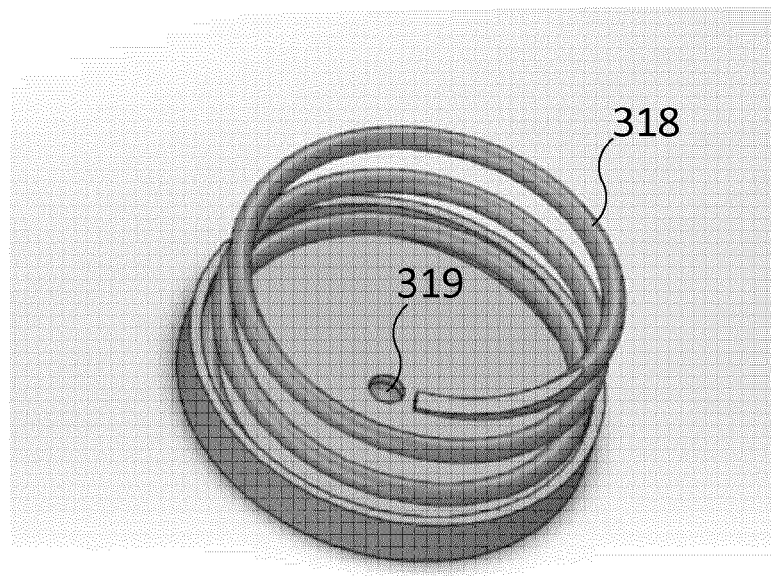

Now referring to FIG. 14A-14B, there is shown an embodiment of a base 315 for the headband sensors 310. The base 315, or dynamech, comprises a body 316 onto which the electrode is secured, and a spring 318 or another biasing means (e.g., any piece of material with elastic deformation properties, or an electromagnetic biasing device) that ensures the electrodes can protrude more or less depending on circumstances. The spring 318 is useful for adapting the protruding distance of the electrodes outside the flexible band 210. A female connector 319 is being formed in the base 315 for mechanically receiving (e.g., in a snap-fit relationship) and electrically connecting a male connector 311 of the headband sensors 310. If a snap-fit connection is made between the pin and the bore, then the headband sensors 310 can be removably secured (i.e., insertable and removable by the user) in sockets formed within the flexible band 210, each one of the sockets having the base 315 at their bottom. The base 315 is then electrically connected to electronics within the headphone 10 for actual data collection.

The purpose of the base 315 is to ensure that the electrode is adjusted to the right height with respect to the flex band, in order to penetrate the user's hair and make contact with their scalp. The secondary purpose is to transfer the signal from the electrode to the active PCB.

In order to penetrate the hair of the users, the electrode legs protrude below the flex band. Since the thickness of people's hair varies from person to person, the length by which the electrode protrudes below the band must vary. User testing confirmed that the compressed thickness of people's hair with respect to the top of their head varies from 0 mm (bald) to 6 mm (thick hair). The base 315 adjusts the height of the electrode legs by allowing the electrode to retract into the band by up to 6 mm (which is thus the maximum protrusion length). This is the primary requirement of the base 315. The spring 318 allows the electrode to retract into the band when force is applied by the user's head. When the headphones are worn, the spring would automatically compress to the appropriate height for the given user's head.

The secondary requirement is that the base 315 must conduct the signal from the electrode (which measures the EEG from the user's scalp) to the active PCB. This may be accomplished by the base 315 itself, or by a separate conductor part.

Figure 15:
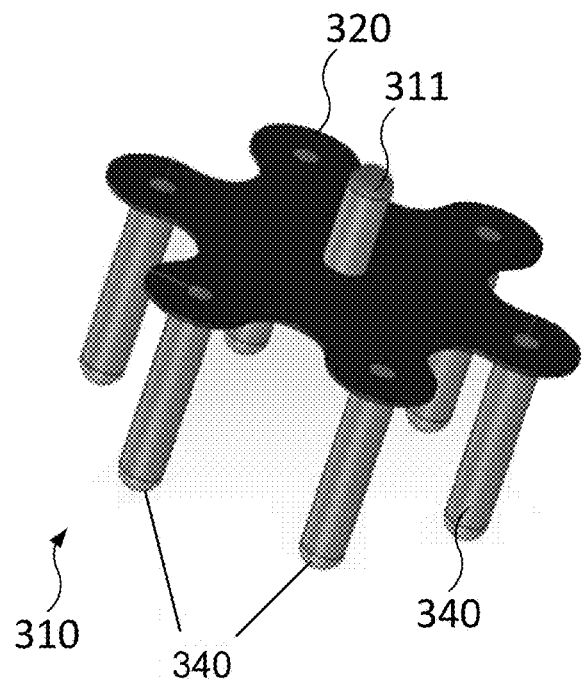
FIG. 15 is a perspective view illustrating a headband electrode, according to an embodiment.

Now referring to FIG. 15, there is shown an embodiment of a headband electrode 310 as used on the flexible band and to be applied onto the scalp of the user.

Figure 16A:
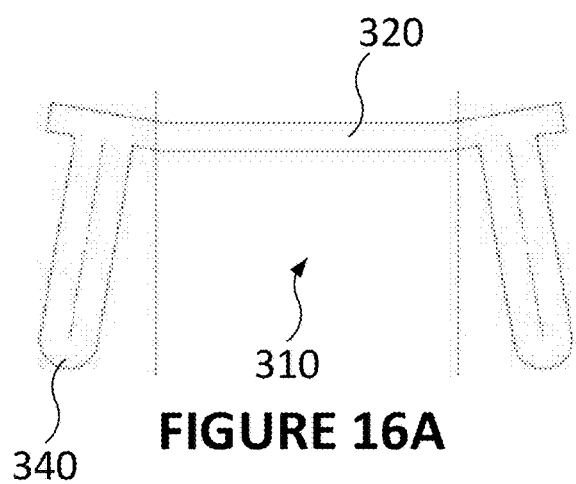
FIGS. 16A-16B are side views illustrating a headband electrode at rest and deformed under a force, respectively, according to an embodiment.
Figure 16B:
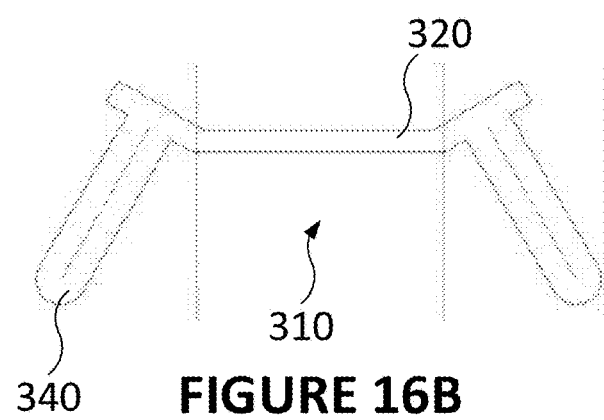

According to an embodiment, the headband sensors 310, or electrodes, comprise a flexible substrate 320 to which legs 340 are attached. The flexible substrate 320 can be made of either polymer or a thin portion of metal. Using a polymer, or a thin surface of metal, ensures that the flexible substrate 320 is flexible, especially more flexible than the legs 340. It means that under the weight of the headphone (which normally has a mass in the order of magnitude of a few hundred grams), when the headband sensor 310 contact and urges on the user's head, the legs 340, which are more rigid (or less flexible) than the flexible substrate 320, will spread (i.e., the rod-shaped leg will change orientation compared to the original orientation which is perpendicular to the flexible substrate 320) while not particularly changing shape. This spread means that the base of the legs 340 is allowed to change orientation, i.e., that the flexible substrate 320 holding the proximal end of the leg is deformed under such a force to put into effect the independent change of orientation of each one of the legs 340. The flexible substrate 320 offers some symmetry and has a diameter of about 16 mm, or between 14 mm and 18 mm, or between 12 mm and 20 mm. FIGS. 16A and 16B illustrate, for an exemplary two-leg sensor, a pair of leg in an original position and in a spread position, respectively. A male connector 311 extends from the flexible substrate 320 in a direction contrary to that of the legs 340.

According to an embodiment, the legs, or pins, are made of metal, to be both electrically conductive and preferably rigid (i.e., not substantially flexible in comparison with the flexible substrate 320). The legs of the electrode can be gold-plated, or plated with or made of other materials such as silver, silver/silver chloride, tin, stainless steel, or platinum, in order to provide a corrosion-free contact interface with the skin, since the scalp is a high-salt environment. The legs fit through the user's hair to maintain contact with the user's scalp, while the flexible substrate acts as a spring mechanism, or adaptive base for the legs 340, to equalize the force between the legs 340 and allow each one of them to undergo an independent angular movement (i.e., spread) with respect to the flexible substrate 320, and maintain contact for each one of the legs 340 with the scalp in response to movement of the headphone 10 on the user's head.

The legs 340 of the headband electrodes 310 have a diameter which is small enough to fit through the user's hair. According to an embodiment, there leg has a diameter of about 2 mm, or between 1.8 mm and 2.2 mm, or between 1.5 mm and 2.5 mm. The bottom (i.e., distal end with respect to the flexible substrate 320) of each leg is curved in such a way as to maximize the contact surface area of the electrode on the user's skin. The legs 340 may be either rigid or flexible. According to an embodiment, they are rather rigid and have a stiffness of about 50 g/mm. The electrode legs 340 may move independently from each other, in order to allow for a consistent contact on an irregular surface.

The length of the legs 340 should be slightly longer than the desired protrusion length of the legs. For example, a length of 7.4 mm is appropriate to provide the protrusion length of maximum 6 mm. Otherwise, a length between 6 mm and 8 mm, or between 4 mm and 9 mm, or between 2 mm and 9 mm, would be appropriate and provide a protrusion length of about 1.5 mm shorter.

According to an embodiment, a printed FPC can be used as the conductive substrate, since it provides the required flexibility while maintaining the ability to conduct the signal through. Alternative designs may instead use a copper plate, conductive rubber, steel, or any comparable conductor. The legs can be soldered to the substrate, but any comparable electrical connector is suitable.

According to an embodiment, the electrode is replaceable by the user. As such, the electrode should be easy to insert or remove from the base 315, inserting and ensuring an adequate electrical connection. The electrode should also be stable enough to be manipulated by hand without breaking or plastically deforming. A friction connector can be provided with the base 315, for example a connection similar to an RCA cable, i.e., a rigid conductive pin sliding into a flexible insert. Any alternative connector is equally suitable, so long as the resulting fit in tight enough to prevent the electrode from bending at the connector joint, or falling out of the socket formed within the flexible band 210.

According to an embodiment, the headphone 10 provides additional sensors, namely earcup sensors 360 on the earcup 400, since collecting data from this region by the ears may be useful in some circumstances. The earcup sensors 360 comprise a conductive material (conductive fabric or polymer, or metal) embedded in the inside of the earcup foam, which can be sewn thereto. The earcup sensor 360 is located at a location on the earcup 400 which allows for making a mechanical (and thus electrical) contact with the back of the user's ear, near the mastoid. The earcup sensor 360 may also comprise a rigid or semi-rigid protrusion on the inside of the earcup 400, which contacts the top or back of the user's ear while the headphones 10 are worn.

Figure 22:
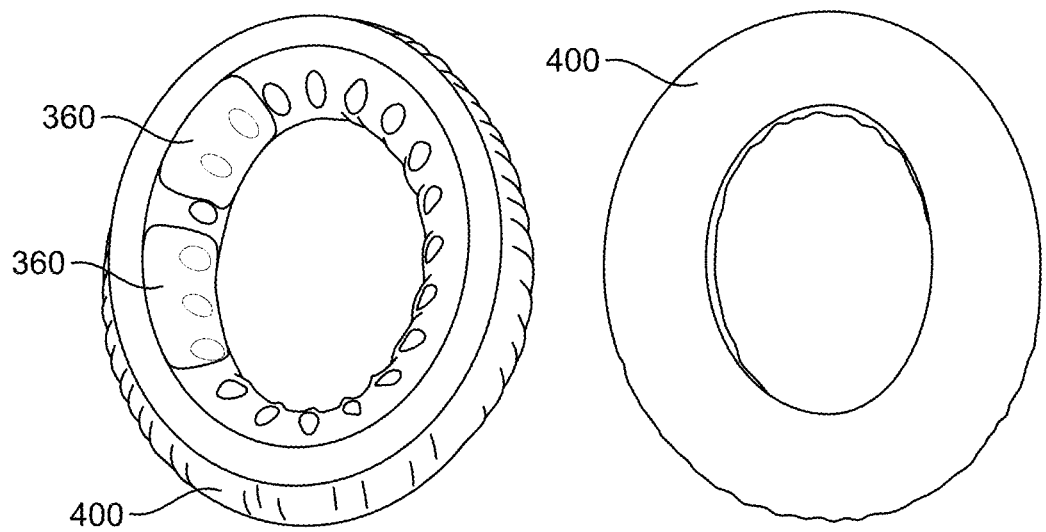
FIG. 22 is a side view illustrating electrodes on an outward surface and an inward surface of an earcup, according to an embodiment.
Figure 23:
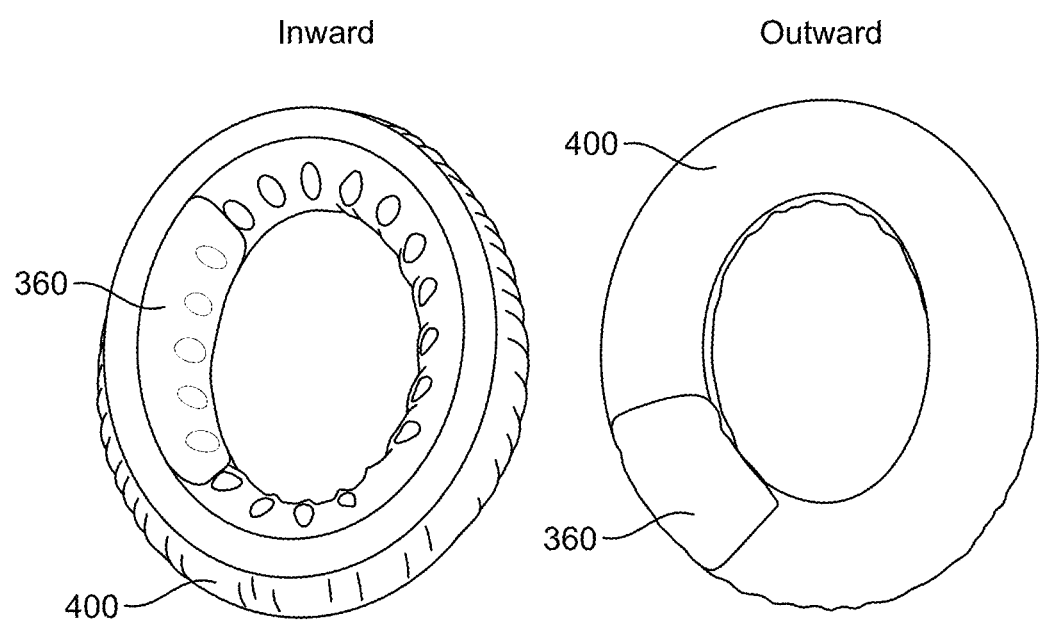
FIG. 23 is a side view illustrating electrodes on an outward surface and an inward surface of an earcup, according to another embodiment.

As shown in FIGS. 22 and 23, illustrating an inward surface (left) and an outward surface (right) of an earcup, where the outward is the portion of the earcup that contacts the head of the user, and in inward is directed toward a rear surface of the ears. As shown in FIG. 22, the earcup sensors 360 can be provided on a rear surface on at least one earcup 400, i.e., a dual back arrangement, where a first earcup sensor is located at an upper rear location and a second earcup sensor is located at a lower rear location on the inward side of the earcup 400, where they are expected to contact a similarly located area of the rear surface of the ear. Alternatively, as shown in FIG. 23, there can be provided earcup electrodes 360 on the two sides of at least one of the earcups (back and front, or outward/inward arrangement). This second embodiment covers a greater total surface area but introduces greater complexity as a conductive fabric needs to be sewn on the inward area of the earcups, where it will be in contact with the user head (i.e., the mastoid area), and also exposed to damage. Moreover, outward earcup electrodes 360 can be less performant if the user has hair by the mastoid area, where such an electrode is to be in contact. Inward earcup electrodes 360 are not affected by hair, as there is none on the rear surface of the ear.

The earcup 400 curves around the user's ear (i.e., it is circumaural), maintaining contact with the back of the mastoid. According to an embodiment, the earcup comprises foam. The earcup 400 is smaller than typical prior-art circumaural ear cups (i.e., the type of earcup that surrounds the ear), which typically do not contact the user's ear. It is also larger than typical prior-art on-ear cups, which compress the ear and do not surround it. The earcup 400, according to an embodiment of the invention, thus has a size that would be considered, in the prior art, as an in-between situation which would not be desirable, whereas it is used in the present headphone 10 to ensure proper contact between an inside portion of the earcup and an outside portion of the ear where electrical contact by the sensor 360 may be desirable.

Figure 17:
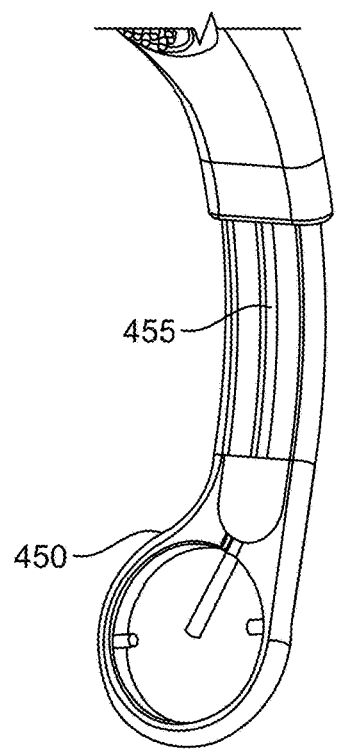
FIG. 17 is a perspective view illustrating an armband for holding the earcups, according to an embodiment.
Figure 18:
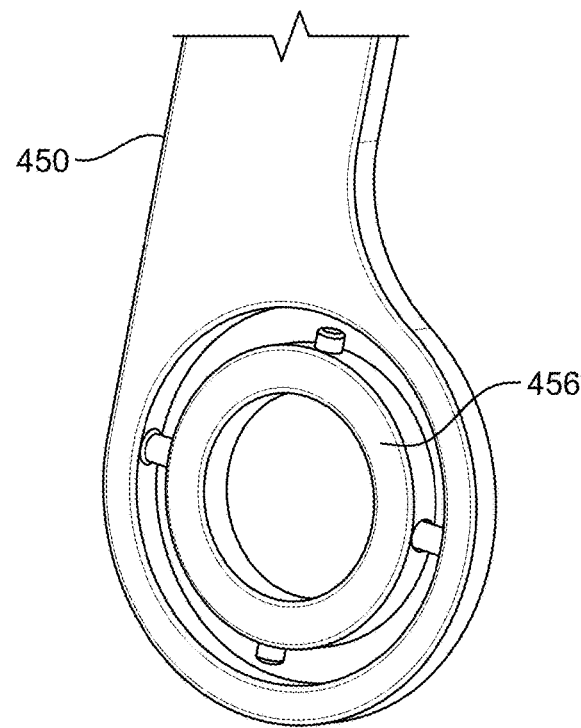
FIG. 18 is a perspective view illustrating a pivot member within an armband for holding the earcups, according to an embodiment.
Figure 19:
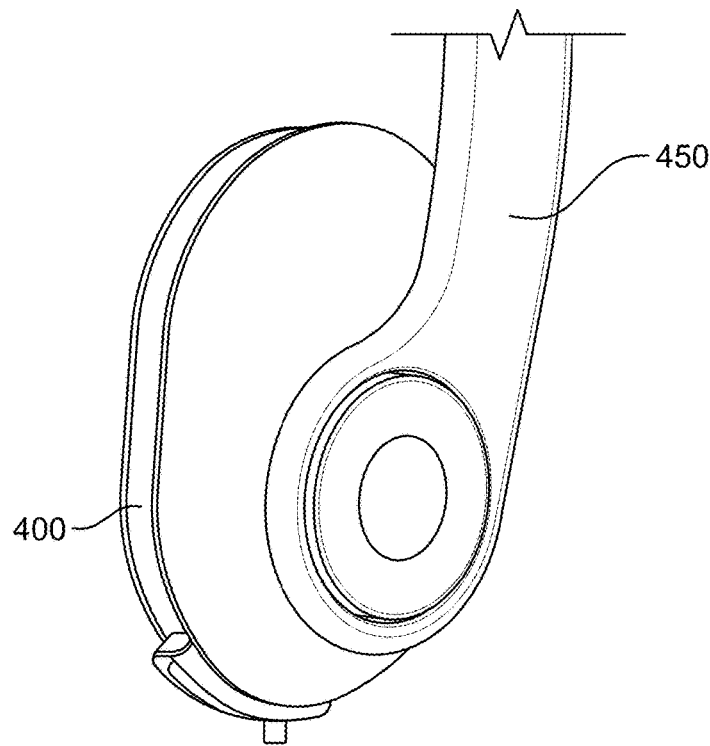
FIG. 19 is a perspective view illustrating a pivotable earcup, according to an embodiment.

The armband or earcup holder 450 is shown in FIG. 17. According to an embodiment, the earcup holder 450 may comprise a sliding rail 455 or any other means by which the overall length can be adjusted up to certain limits by raising or lowering the earcups. Compared to the prior art, the sliding rail should comprise a stopper that prevents the earcup holder to impact the flexible band 210. As shown in FIGS. 18-19, the earcup holder 450 can comprise a pivoting member 456 which can comprise for example two pivots, such as a mastoid pivot and a sagittal pivot, allowing rotation of the earcup 400 along these axes for better contact of the earcup sensors 360 with the ear of the user when being worn.

Figure 20:
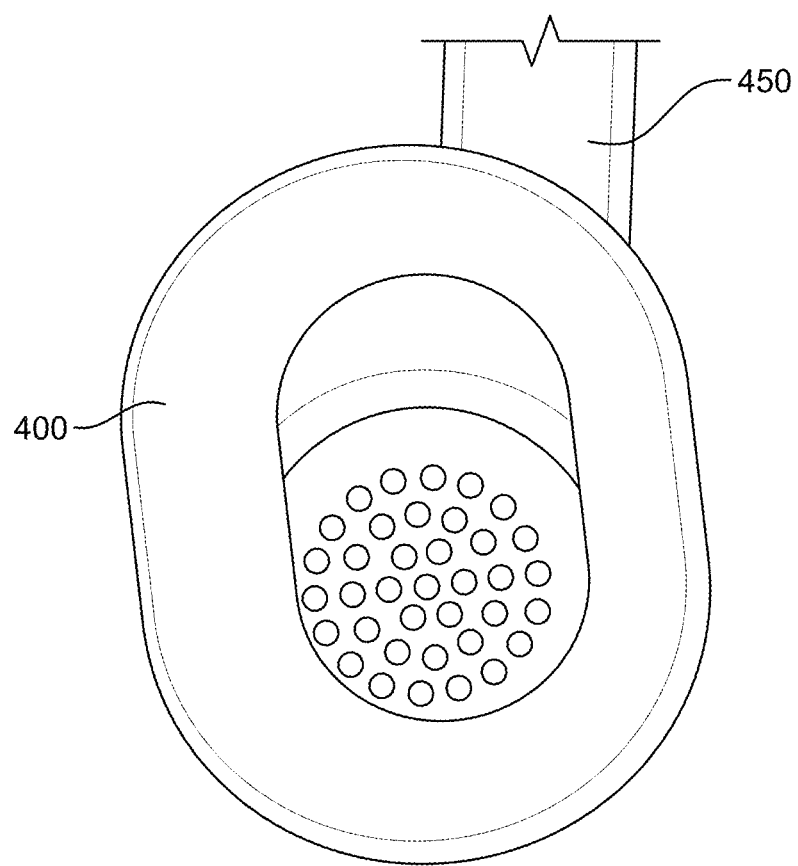
FIG. 20 is a side view illustrating the inclination of the earcup, according to an embodiment.

According to an embodiment, the earcup 400 is asymmetric, such that a small lip tucks behind the user's ear when it is being worn. The radius of this lip can be chosen to match the gap between the user's ear and the mastoid, caused by the auriculocephalic angle of the ear, as shown in FIG. 20. The foam should contact the user's ear primarily at the back of the ear. Contact along the top of the ear is permitted, so long as the applied pressure does not cause discomfort, but is not necessary. The radius of the point of contact between the foam and the ear can be about 5 mm, to ensure that contact is made across a range of ear shapes.

Figure 21A:
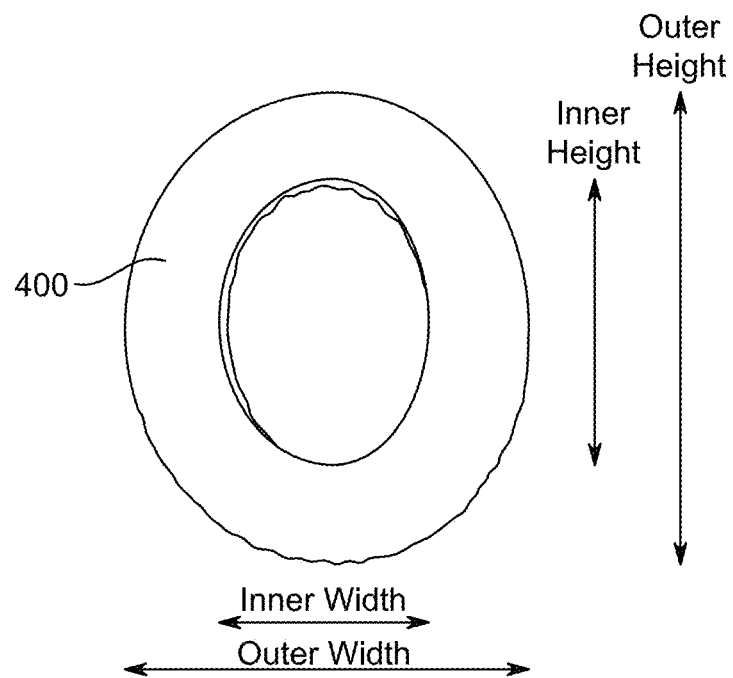
FIG. 21A is a side view illustrating definitions of a shape of the earcup, according to an embodiment.
Figure 21B:
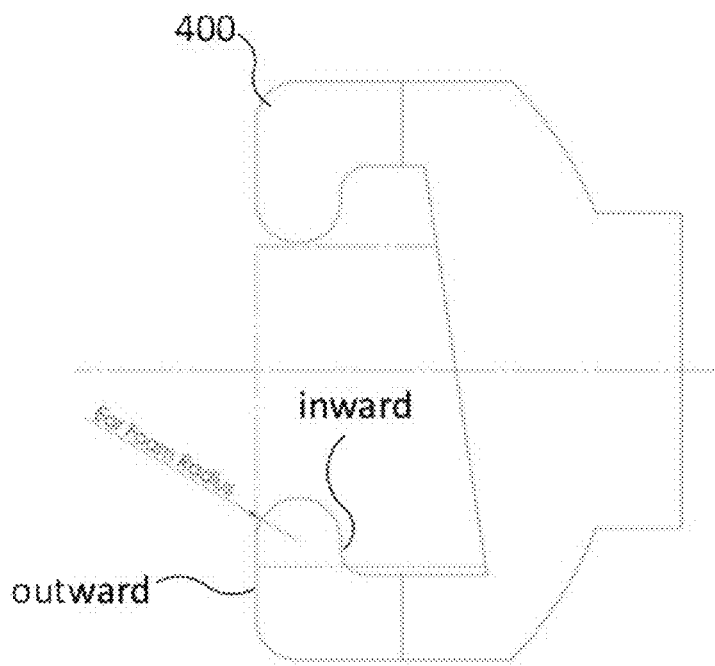
FIG. 21B is a top view illustrating the inside of an earcup, according to an embodiment.

FIGS. 21A-21B illustrate the shape of the foam piece of the earcup, and further illustrate that the foam piece of the earcup is shaped to reach the region behind the ears. According to an embodiment, the inner width is about 30 mm, the outer width is about 68 mm, the inner height is about 60 mm and the outer height is about 98 mm.

There is now described electronic filters which can be advantageously provided in an embodiment of the headphones to filter noise and eventually enhance signal quality for later analysis.

According to an embodiment, each electrode (headband electrodes 310 and earcup electrodes 360) has a direct electrical connection to a high-impedance voltage follower circuit, which buffers the incoming EEG signal. The buffer circuit is subsequently connected to a series of passive and active filter circuits, which de-noise the signal, and then to a high-gain amplification circuit. Finally, each channel passes through an analog to digital converter, before being sent to the computer via Bluetooth or USB. A protection circuit can be added to protect the circuitry from electrostatic discharges by limiting current below 1 µA.

According to an embodiment, the printed circuit board (PCB) layout comprises components which implement several preconditioning techniques optimized for EEG signals. These can include, without limitation:
using oxygen-free copper planes;
shielding components with a copper cover, which can passive or active during the signal preconditioning;
choosing materials for the passive components for their specific properties, among the following:
  a. silver mica for active filter capacitors;
  b. tantalum and metal film for power supply decoupling; and
  c. metal film or wire wound resistors for noise reduction;
PCB traces use a combination of copper-gold; copper silver; copper silver and gold in specific percentages to improve signal-to-noise ratio.

Within the headphone 10, different components can be added, during assembly, in order to limit noise interference during data collection by the sensors, notably, and without limitation:
wire shielding and analog ground plan isolation in order to limit noise interference and parasitic capacitance; or a combination of a triaxial cable and an optical fiber to guarantee superior noise immunity.

There is now described an embodiment of a method implemented on a computing system, in communication with the sensors, that performs operations on the signals collected by the sensors to extract meaning information therefrom.

Figure 24:
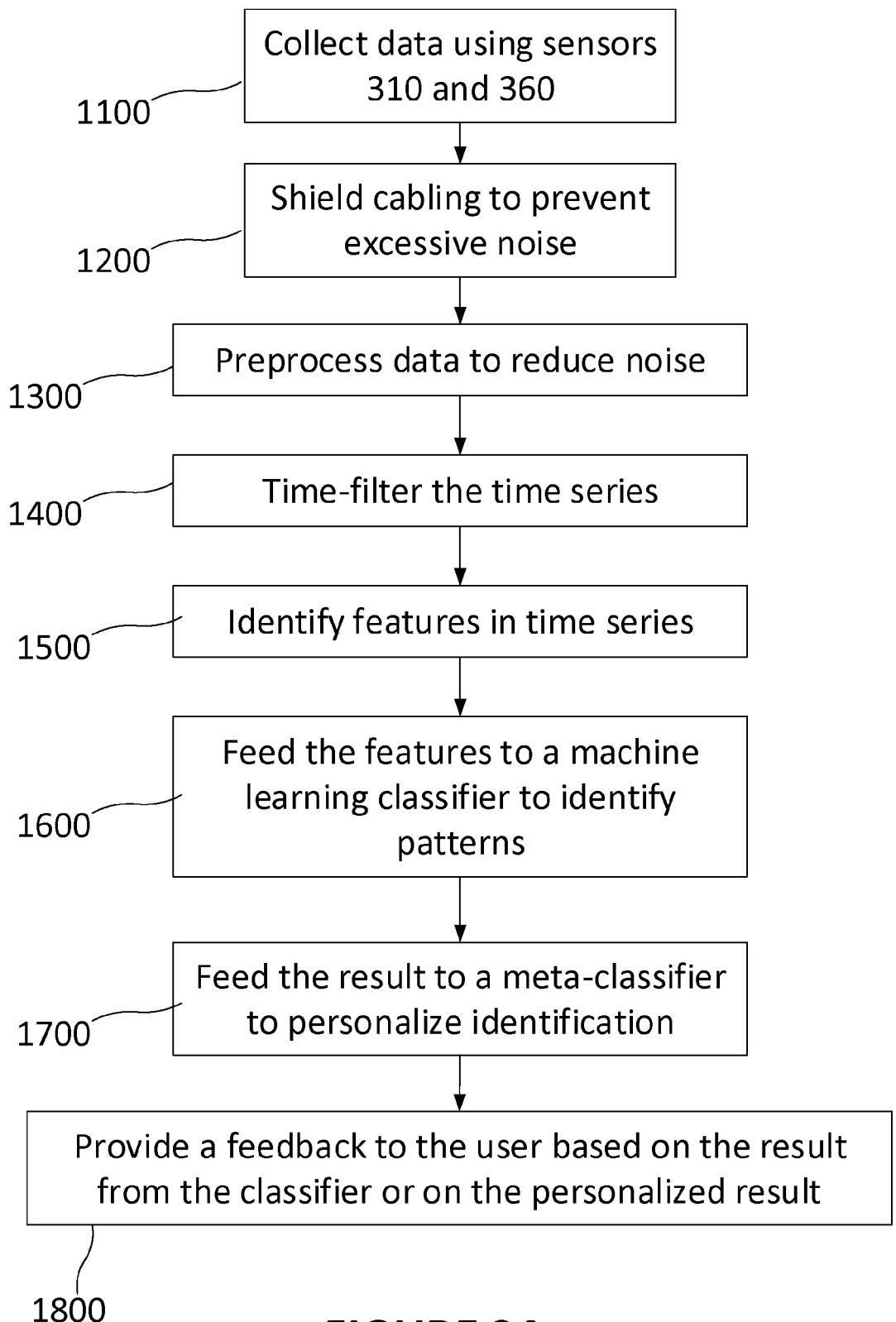
FIG. 24 is flowchart illustrating a method collecting data with EEG sensors and extracting meaningful information from the data, according to an embodiment.

According to an embodiment, and referring to the flowchart of FIG. 24, the data collected by the sensors (step 1100) and routed with the headphone 10 where noise-reduction components are provided (step 1200) are then processed by an embedded processor or sent (preferably wirelessly over a network, or with a wired connection) to a remote computer system in order to implement algorithms for data treatment to extract meaningful information therefrom.

A combination of signal processing, machine learning, and artificial intelligence can be implemented to deliver meaningful results, such as accurate predictions of user concentration from low-dimensional noisy EEG data.

Collected EEG signals are first preprocessed. (step 1300) The preprocessing can include, for example, blind source separation algorithms, including PCA, ICA, and wavelet decomposition, and extraction of separable noise sources, including eye blinks and muscle artifacts. According to an embodiment, thresholding is used to identify critical noise sources which are non-separable.

According to an embodiment, the signals are time-filtered (step 1400) using several low and high-order digital FIR and IIR filters to remove high frequency artifacts, low frequency and DC noise sources, powerline noise, and other frequency-based sources of non-EEG noise.

According to an embodiment, the EEG signal, after preprocessing, is separated into features using several signal processing techniques (step 1500). Time-frequency features such as FFT, phase delay, cepstral coefficients, and wavelet transforms can be extracted, for example by applying sliding bins across the time-series data. According to an embodiment, energetic features such as hjorth parameters and zero crossing rate are calculated over windowed bins. Structural information features such as Shannon entropy and Lyapunov exponents are also calculated. These features are measured on each EEG channel, or any linear or nonlinear combination of each channel. The extracted EEG features can be left unprocessed, or can be post-processed using statistical methods, such as smoothing, derivatives, or weighted averaging.

According to an embodiment, in order to describe the state of the person wearing the headphones 10, the features previously identified can be fed into a series of machine learning classifiers (step 1600), which are trained on subsets of the collected data. These classifiers include but are not limited to LDA, SVM, neural networks, decision trees, etc. As a result, each classifier develops the ability to differentiate unique patterns in the EEG signal.

According to an embodiment, these classifiers are fed into a boosted meta-classifier (step 1700), which takes the output of the individual classifiers as inputs. This meta-classifier can be trained on an individual's data, to tailor the classifier system to their unique input and individualize the descriptions or predictions. According to an embodiment, the output of the classifier system is fed into a reinforcement learning model, which determines the likelihood that the user is distracted. The user's state of concentration and distraction is modeled as a Markov decision problem, which the algorithm learns to navigate through use of structures such as Qlearning, and TD difference learning.

Feedback can eventually be provided to the user, as described above in relation with the embodiment of FIG. 1 (step 1800).

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. Headphones comprising:
   earcups to be placed about ears of a user;
   a headband linking the earcups and extending above a head of the user;
   a flexible band distinct from the headband such as to flex independently therefrom and secured below the headband for contact with the head of the user; and
   headband electrode sockets formed within the flexible band for receiving headband electrodes, each headband electrode socket having an electrically conductive base, the electrically conductive base comprising a body onto which a headband electrode is secured and a spring for adapting a protruding distance of the headband electrode outside of the flexible band.

2. The headphones of claim 1, wherein the flexible band has a shape at rest not conforming with the head by providing the flexible band with a radius of curvature larger than a radius of curvature of a top area of a human head.

3. The headphones of claim 2, wherein the flexible band has a flexibility which makes the flexible band deform under a weight of the earcups to conform with the head of the user.

4. The headphones of claim 1, wherein the flexible band has a shape at rest characterized by a radius of curvature between 85 mm and 100 mm, and is made of a resilient material which under the weight of the headphones, which is between 100 g and 1 kg, adopts a radius of curvature between 70 mm and 85 mm.

5. The headphones of claim 3, wherein the flexible band is deformable under the weight of the earcups to conform with the head of the user, while the headband does not substantially flex.

6. The headphones of claim 1, further comprising the headband electrodes to be embedded in the headband electrode sockets of the flexible band and having a portion thereof protruding downwardly from the flexible band.

7. The headphones of claim 6, wherein the headband electrodes comprise a flexible substrate and a plurality of legs extending therefrom and protruding from the flexible band.

8. The headphones of claim 7, wherein the flexible substrate is both electrically conductive and flexible such as to allow the legs to change orientation with respect to the flexible substrate.

9. The headphones of claim 7, wherein each of the headband electrodes comprises a male connector to fit with a corresponding female connector within the electrically conductive base of a corresponding one of the headband electrode sockets to hold the headband electrodes in the headband electrode sockets and form an electrical connection between the legs and the electrically conductive base within the headband electrode sockets.

10. The headphones of claim 6, wherein the headband electrodes are user-detachable from the electrically conductive base without having to dismount the flexible band.

11. Headphones comprising:
    earcups to be placed about ears of a user;
    a headband linking the earcups and extending above a head of the user;
    a flexible band distinct from the headband and secured below the headband for contact with the head of the user;
    headband electrodes each embedded in an electrically conductive base located in a headband electrode socket of the flexible band, the electrically conductive base comprising a body onto which a headband electrode is secured and a spring for adapting a protruding distance of the headband electrode outside of the flexible band; and
    earcup electrodes on the earcups for contact with a rear surface of an ear of the user.

12. The headphones of claim 11, wherein the earcup electrodes comprise conductive fabric.

13. The headphones of claim 12, wherein the earcup electrodes for contact with the rear surface of the ear are on an inward surface of the earcup directed toward the rear surface of the ear.

14. The headphones of claim 13, wherein the earcup electrodes for contact with the rear surface of the ear comprise an upper rear earcup electrode and a lower rear earcup electrode, respectively located at an upper rear location and a lower rear location on the inward surface of at least one earcup.

15. The headphones of claim 13, further comprising an outward earcup electrode provided on an outward surface of the earcup directed toward the head, in a region of mastoid when the headphones are worn.

16. A method for collecting EEG data, the method comprising:
    laying onto a head of a user a headband of headphones, the headband linking earcups;

contacting with the head of the user a flexible band distinct from the headband and secured below the headband;

letting the flexible band adopt a shape of a portion of the head of the user under the weight of the earcups;

contacting headband electrodes with a scalp of the user, the headband electrodes being embedded in headband electrode sockets, each headband electrode socket having an electrically conductive base, the electrically conductive base— having a body and a spring, a protruding distance of the headband electrodes outside of the flexible band being adapted by the spring of the electrically conductive base; and collecting data from the headband electrodes.

17. The method of claim 16, further comprising collecting data from earcup electrodes located on a surface of the earcups.

18. The method of claim 16, further comprising identifying features in the collected data within time windows of the collected data and upon identifying the features, feeding the features to a machine learning classifier to identify patterns in the features.

19. The method of claim 18, wherein pattern identification comprises determining a state of concentration and upon identification of the patterns, feeding the patterns to a meta-classifier to personalize pattern identification.

20. The method of claim 19, further comprising upon determining a state of concentration, providing a feedback to the user, the feedback being dependent on the state of concentration as determined and wherein providing the feedback comprises determining a moment when to provide the feedback that is expected to maximize an effect of the feedback to the user.

* * * * *